United States Patent
Sachs et al.

(10) Patent No.: US 9,211,313 B2
(45) Date of Patent: Dec. 15, 2015

(54) METHODS AND COMPOUND TO INHIBIT $CA^{2+}$ PERMEABLE CATION CONDUCTANCE

(75) Inventors: Frederick Sachs, Buffalo, NY (US); Philip Gottlieb, Buffalo, NY (US); Thomas Suchyna, Amherst, NY (US); Seth L. Alper, Boston, MA (US); David H. Vandorpe, Watertown, MA (US); Chang Xu, Mount Kisco, NY (US)

(73) Assignees: The Research Foundation of State University of New York, Amherst, NY (US); Beth Israel Deaconess Medical Center, Boston, MA (US)

(*) Notice: Subject to any disclaimer, the term of this patent is extended or adjusted under 35 U.S.C. 154(b) by 499 days.

(21) Appl. No.: 13/351,611

(22) Filed: Jan. 17, 2012

(65) Prior Publication Data

US 2012/0184491 A1 Jul. 19, 2012

Related U.S. Application Data

(60) Provisional application No. 61/432,640, filed on Jan. 14, 2011.

(51) Int. Cl.
*A61K 38/16* (2006.01)
*A61K 38/17* (2006.01)

(52) U.S. Cl.
CPC .................................. *A61K 38/1767* (2013.01)

(58) Field of Classification Search
CPC ................................................. A61K 38/1767
See application file for complete search history.

(56) References Cited

U.S. PATENT DOCUMENTS

| | | | |
|---|---|---|---|
| 4,925,664 A | 5/1990 | Jackson et al. | |
| 5,756,663 A | 5/1998 | Lampe et al. | |
| 5,968,838 A | 10/1999 | Lampe et al. | |
| 6,261,569 B1 | 7/2001 | Comis et al. | |
| 7,125,847 B1 * | 10/2006 | Sachs et al. | 514/16.4 |
| 7,259,145 B2 * | 8/2007 | Sachs et al. | 514/16.4 |
| 7,396,816 B2 * | 7/2008 | Yokotagawa et al. | 514/16.4 |
| 7,709,533 B2 | 5/2010 | Wang et al. | |
| 7,718,641 B2 * | 5/2010 | Vohra et al. | 514/183 |

FOREIGN PATENT DOCUMENTS

| | | | |
|---|---|---|---|
| WO | 01/76618 A1 | 10/2001 | |
| WO | WO 01/76618 | * 10/2001 | ............. A61K 38/16 |
| WO | 2004/085647 A1 | 10/2004 | |

OTHER PUBLICATIONS

Vandorpe et al., Jan. 2010, Hypoxia Activates a Ca+-Permeable Cation Conductance Sensitive to Carobn Monoxide and to GsMTx-4 in Human and Mouse Sickle Erythrocytes, PLoS One, 5(1): 14 pages.*
Stocker et al., 2003, ICA-17043, a novel Gardos channel blocker, prevents sickled red blood cell dehydration in vitro and in vivo in SAD mice, Blood, 101(6): 2412-2418.*
Bennekou et al., 2001, Treatment with NS3623, a novel Cl-conductance blocker, ameliorates erythrocyte dehydration in transgenic SAD mice: a possible new therapeutic approach for sickle cell disease, Blood, 97(5): 1451-1457.*
Rhoda et al., 1990, Ca2+ Permeability in Deoxygenated Sickle Cells, Blood, 75(12): 2453-2458.*
Gibson et al., 2000, Effect of dimethyl adipimidate on K+ transport and shape change in red blood cells from sickle cell patients, FEBS Letters, 480: 179-183.*
Khan et al., 2004, Oxygen dependence of K+-Cl- cotransport in human red cell ghosts and sickle cells, Bioelectrochemistry, 62: 141-146.*
Hannermann et al., 2014, Effects of 5-hydroxymethyl-2-furfural on the volume and membrane permeability of red blood cells from patients with sickle cell disease, J. Physiol, 592(18): 4039-4049.*
Gottlieb, P., et al., Mechanosensitive Ion Channels as Drug Targets, Current Drug Targets—CNS & Neurological Disorders, Aug. 2004, vol. 3, No. 4, pp. 287-295.
Suchyna, T., et al., Bilayer-dependent inhibition of mechanosensitive channels by neuroactive peptide enantiomers, Nature, Jul. 8, 2004, vol. 420, pp. 235-240.
Craik, D., et al., The cystine knot motif in toxins and implications for drug design, Toxicon, vol. 39, 2001, pp. 43-60.
Suchyna, T., et al., Identification of a Peptide Toxin from Grammostola spatulata Spider Venom that Blocks Cation-selective Stretch-activated Channels, J. Gen. Physiol., May 2000, vol. 115, pp. 583-598.
Nazir, S., et al., Effects of G. spatulata Venom, a Novel Stretch-activated Channel Blocker in a Model of Stretch-Induced Ventricular Fibrillation in the Isolated Heart, Abstracts Frm the 68th Scientific Sessions, Oct. 15, 1995, vol. 2 (Suppl. 1) p. 641.

* cited by examiner

*Primary Examiner* — Amber D Steele
(74) *Attorney, Agent, or Firm* — Hodgson Russ LLP

(57) ABSTRACT

The present invention provides methods and compositions for inhibiting calcium permeable cation conductance of red blood cells from individuals afflicted with sickle cell anemia. The method comprises exposing the cells to the peptide GsMTx4 and/or variants thereof.

8 Claims, 15 Drawing Sheets

// METHODS AND COMPOUND TO INHIBIT CA²⁺ PERMEABLE CATION CONDUCTANCE

CROSS REFERENCE TO RELATED APPLICATIONS

This application claims the priority to U.S. Provisional application No. 61/432,640, filed on Jan. 14, 2011, the disclosure of which is incorporated herein by reference.

STATEMENT REGARDING FEDERALLY SPONSORED RESEARCH OR DEVELOPMENT

This invention was made with government support under Grant Nos. HL077765, HL15157, and HL071797 from the National Institutes of Health. The Government has certain rights in the invention.

FIELD OF THE INVENTION

This invention relates to the use of compositions comprising inhibitors of mechano sensitive channels for treating or reducing the severity of sickle cell anemia.

BACKGROUND OF THE INVENTION

Sickle cell disease is caused by the homozygous missense mutation of Glu to Val in codon 6 of the hemoglobin (Hb) β chain gene, encoding the mutant βS globin polypeptide. In the absence of wildtype β globin, assembly of tetrameric α2βS2 generates sickle hemoglobin (HbSS). Polymerization of deoxy-HbSS leads to oxidation, crosslinking, stiffening, and distortion of the red cell membrane, increased adhesiveness to leukocytes and to endothelial cells, and cell lysis. The resulting hemolytic anemia and diffuse vaso-occlusive pathology causes life-long illness for which the only currently approved chronic drug treatment is hydroxyurea, supplementing the traditional mainstays of symptomatic treatment: hydration, pain relief, anti-inflammatory drugs, and antibiotics. Marrow transplantation can be curative, but the associated morbidity remains high enough to discourage its widespread use even in developed countries. Although gene therapy continues to show promise, development of adjunct pharmacotherapy remains a high priority for treatment and management of sickle disease.

It has been reported that mature human sickle red cells (SS cells) are dehydrated by inappropriate hypoxic activation of erythroid K—Cl cotransporters and of the erythroid $Ca^{2+}$ activated $K^+$ channel KCa3.1/IK1/KCNN4, also known as the "Gardos channel" (Brugnara et al. 2001, Drug news & perspectives 14(4): 208-220; Steinberg and Brugnara 2003, Annual review of medicine 54: 89-112; Begenisich et al. 2004, The Journal of biological chemistry 279(46): 47681-47687; Rust et al. 2007, The Journal of clinical investigation 117(6): 1708-1717). The consequent elevation of intracellular [HbSS] dramatically shortens the "delay time" (Mozzarelli et al. 1987, Science (New York, N.Y. 237(4814): 500-506) for assembly of the critical aggregate of deoxy-HbSS tetramers required for subsequent rapid growth of deoxy-HbS fiber length (Christoph et al. 2005, Biophysical journal 88(2): 1371-1376). Current therapeutic approaches involve inhibition of erythroid K—Cl cotransporters with magnesium pidolate (Hankins et al. 2008, British journal of haematology 140(1): 80-85), the KCa3.1 inhibitor ICA-17043 (senicapoc) (Ataga et al. 2008, Blood 111(8): 3991-3997) and endothelin antagonists (Sabaa et al. 2008, The Journal of clinical investigation, Vol. 118(5):1924-33).

SUMMARY OF THE INVENTION

In the present invention, we show by cell-attached and nystatin-permeabilized patch clamp recording from mammalian sickle erythrocytes that deoxygenation reversibly activates a $Ca^{2+}$ and cation-permeable conductance and that this activation can be inhibited by an inhibitor of stretch-activated cation channel, Grammastola spatulata mechanotoxin4 (GsMTx4) and variants thereof. Other inhibitors of the activation include dipyridamole and carbon monoxide. Deoxygenation also elevates sickle erythrocyte $[Ca^{2+}]_i$, in a manner similarly inhibited by GsMTx4 and by carbon monoxide. Normal mammalian erythrocytes did not exhibit these responses to deoxygenation. Deoxygenation-induced elevation of ($[Ca^{2+}]_i$) in mouse sickle erythrocytes did not require KCa3.1 activity.

The data provide electrophysiological and fluorimetric evidence in sickle erythrocytes of mouse and human for a deoxygenation-induced, reversible, $Ca^{2+}$-permeable cation conductance blocked by inhibition of HbSS polymerization and by an inhibitor of stretch-activated cation channels. This cation permeability pathway is likely an important source of intracellular $Ca^{2+}$ for pathologic activation of KCa3.1 in sickle erythrocytes. Blockade of this pathway represents a therapeutic target for the treatment of sickle disease.

The present invention provides a method for treating or preventing one or more symptoms of sickle cell anemia disease. The method comprises exposing red blood cells of an individual to a therapeutically effective amount of an inhibitor of hypoxia activated $Ca^{2+}$ and cation-permeable conductance. The exposure may be in vivo or ex vivo (such as through a shunt or during dialysis). In one embodiment, the method comprises administering to an individual afflicted with or likely to be afflicted with, or at risk for sickle cell anemia, a composition comprising a peptide that inhibits a hypoxia activated $Ca^{2+}$ and cation-permeable conductance. An example of such a compound that inhibits hypoxia activated $Ca^{2+}$ and cation-permeable conductance is GsMTx4 and/or its variants. Thus, in one embodiment, the present invention comprises administering to an individual a composition comprising GsMTx4 and/or one or more of its variant to treat or prevent the symptoms of sickle cell anemia or to reduce the severity of one or more symptoms of sickle cell anemia. Additionally, the present invention also provides pharmaceutical compositions comprising GsMTx4 and/or one or more of its variants.

DETAILED DESCRIPTION OF THE INVENTION

Figure 1A:
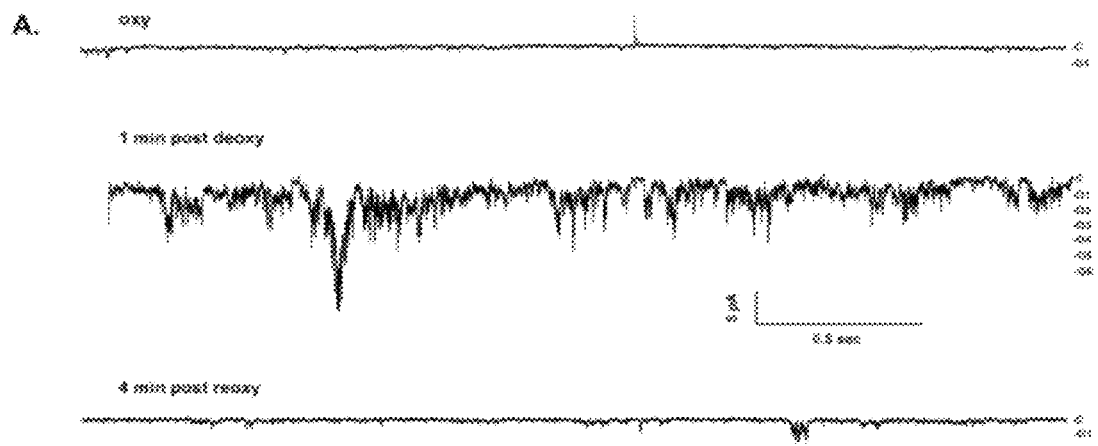
FIG. 1. Deoxygenation reversibly activates a conductance in red cells from transgenic SAD sickle mice. A. Representative current trace from an individual cell-attached patch on a human SS erythrocyte before deoxygenation (upper trace, oxy), 1 min post-deoxygenation (middle trace, deoxy), and 4 min post-reoxygenation (lower trace, reoxy); −Vp=−50 mV. Symmetric pipette and bath solutions contained (in mM) 140 NaCl, 4 KCl, 1CaCl2, 1 MgCl2, 10 Na 4-(2-hydroxyethyl)-1-piperazineethanesulfonic acid (HEPES), pH 7.4. B. Seal resistance was maintained during deoxygenation in all 9 cells, and during reoxygenation in 6 of the 9 cells (*, p<0.01 vs. oxy; p=N.S. vs. re-oxy, ANOVA). C. Summary of patches such as in panel A, showing that the increased NPo (product of the number of single channels and the channel open probability) observed after deoxygenation was reversible (without change in seal resistance) upon reoxygenation (*, p<0.02 vs. oxy; p<0.05 vs. reoxy, ANOVA). Values are means+s.e.m.

The present invention is based on the observation that deoxygenation induced $Ca^{2+}$ and cation-permeable conductance can be inhibited by a mechanosensitive channel blocker. The conductance induced by deoxygenation in on-cell patches of human HbSS red cells and of mouse sickle cells is permeable to $Na^+$, $K^+$, and $Ca^{2+}$, and is inhibited by the mechanosensitive channel blocker GsMTx4, as well as by DIDS and dipyridamole. Inhibition of deoxy-HbSS polymerization by CO also blocks activation of the cation conductance by deoxygenation. Deoxygenation also increased conductance in the nystatin-permeabilized whole cell patch configuration. The deoxygenation-activated conductance is likely responsible for $[Ca^{2+}]_i$ elevation in human and mouse sickle cells, possibly leading to KCa3.1 (Gardos channel) activation and consequent acceleration of pathological sickle cell dehydration.

We found red cells from two mouse models of sickle disease to exhibit deoxygenation-induced currents and $[Ca^{2+}]_i$ elevation with inhibitor sensitivity similar to that in human SS cells. Deoxygenation-induced currents in SAD mouse red cells were completely reversible. SAD mouse red cell membrane patches sustained GΩ seals during transitions from room air to nitrogen, and then back to room air. The initial elevation of $[Ca^{2+}]_i$ elicited by deoxygenation did not require KCa3.1 channel activity, but later phases of $[Ca^{2+}]_i$ elevation were attenuated by absence of KCa3.1 and enhanced by inhibition of the plasmalemmal $Ca^{2+}$ ATPase (PMCA). Human AA allele in red cells and normal mouse red cells exhibited no deoxygenation-induced increases in current or in $[Ca^{2+}]_i$.

These observations extend the phenotypic characterization of deoxygenation-activated $Ca^{2+}$ transport in human sickle red cells, and present the first such data in mouse sickle red cells. The observations include realtime, on-cell and whole cell patch clamp evidence of deoxygenation-induced elevated $Ca^{2+}$ and cation conductance, flourimetric evidence of elevated $[Ca^{2+}]_i$, and description of novel inhibitors of these Psickle-like activities.

In one aspect, the present invention provides a method for inhibiting in a cell, deoxygenation induced $Ca^{2+}$ and cation-permeable conductance. In one embodiment, the cell is a red blood cell. In another embodiment, the red blood cell is a mammalian red blood cell. In another embodiment, the red blood cell is a human red blood cell. The method comprises contacting a cell (such as a red blood cell) with an effective amount of a composition comprising the peptide GsMTx4 or variants thereof.

In another aspect, the present invention provides a method for reducing one or more indications associated with sickle cell anemia. The phrase "indication associated with sickle cell anemia" as used herein means one or more characteristics or symptoms that are associated with the sickle cell anemia disease. Such symptoms include morphological characteristics like sickled red cells, and to activation of the deoxygenation induced conductance permeable to calcium and to other cations (Psickle). Activation of Psickle admits calcium into the sickle cell to activate in turn the calcium-activated potassium channel (Gardos channel/IK1/KCa3.1/KCNN4), and likely also the calcium-activated chloride channel TMEM16A. These activations, in tandem with the activation of electroneural K—Cl cotransporters by the acidic intracellular pH characteristic of the acidotic capillary circulation leads to cellular loss of KCl, reduction of cell volume, and increased intracellular concentration of hemoglobin S. The increased concentration of hemoglobin S slowly progresses through incrementally higher concentrations during repeated episodes of deoxygenation as red cells circulate in the blood. This results in accelerated hemoglobin S polymerization in response to deoxygenation. The method of the invention is accordingly suitable for prophylaxis or therapy of sickle cell disease and can be used for individuals who are at risk for, have been diagnosed with, or are suspected of having sickle cell disease. In one embodiment, the individual to whom a composition of the invention is administered has not been previously treated with an agent that reduces deoxygenation induced calcium and cation permeable conductance in red blood cells. In one embodiment, the individual to whom a composition of the invention is administered has not been previously exposed to GsMTx4, and/or a variant thereof. For therapeutic use, it is desirable that GsMTx4 be used in amounts that have acceptable activity in reducing the deoxygenation induced $Ca^{2+}$ permeable cation channels. 1 microM GsMTx4 applied to the outside of the sickle red cell membrane was observed to completely inhibit deoxygenation-induced $Ca^{2+}$-permeable cation channel activity recorded in the on-cell patch configuration. The same GsMTx4 concentration was observed to nearly completely block the deoxygenation-induced elevation of intracellular free $[Ca^{2+}]$ in sickle red cells. Given the very low to absent toxicity of GsMTx4 in mice, in one embodiment, GsMTx4 or variants of it can be used at concentrations of 0.1 to 10.0 micromolar including all concentrations to the tenth decimal place between 0.1 to 10.0 micromolar. In one embodiment, GsMTx4 or a variant of it is used at a concentration of 0.1 to 10 micromolar in the blood. In another embodiment, the concentration in blood is 0.1 to 5 micromolar and all concentrations therebetween to the tenth decimal place. In another embodiment, the concentration in blood is such that circulating red cells would be exposed to an amount equivalent to 0.1 to 10 micromolar saline concentration used for in vitro exposure. The equivalent amount can be determined by the effect on reducing the deoxygenation induced $Ca^{2+}$ permeable cation channels. Compositions comprising GsMTx4 and/or one or more variants thereof can be administered via any route that will deliver the peptide or peptides to the blood including, but not limited to, inhalation, transdermal, oral, ocular, rectal, transmucosal, intestinal and parenteral administration, including intramuscular, subcutaneous and intravenous injections.

The peptide GsMTx4, as used herein, has the sequence GCLEFWWKCNPNDDKCCRPKLKCSKLFKLCNFSF (SEQ ID NO:1). This peptide is to referred to in this application as GsMTx4 or GsMTx4(34 mer). Substitutions of the last three C-terminal amino acids can be made. Any such amino acid substitution that does not adversely affect the capability of the peptide(s) to inhibit deoxygenation induced $Ca^{2+}$ and cation-permeable conductance in a cell can be made and peptides comprising such substitutions are encompassed within the present invention. Such substitutions can be readily identified by those skilled in the art. In this regard, several substitutions were made and these were found not to affect the properties of the peptide. Therefore, in one embodiment, the peptide of the present invention is GCLEFWWKCNPND-DKCCRPKLKCSKLFKLCNXaaXaaXaa (SEQ ID NO:2). In one embodiment, the amino acid at the $32^{nd}$ position is Y (instead of F) thus providing the sequence GCLEFWWKC-NPNDDKCCRPKLKCSKLFKLCNYSF (SEQ ID NO:3). In another embodiment, the serine at the $33^{rd}$ position can be changed to cysteine, providing the sequence GCLEFW-WKCNPNDDKCCRPKLKCSKLFKLCNFCF (SEQ ID NO:4), and if desired, the cysteine can be derivatized with reporters such as fluorescein. In another embodiment, the phenylalanine at the $34^{th}$ position can be changed to serine and/or another amino acid can be added as the $35^{th}$ amino acid providing the sequence GCLEFWWKCNPNDDKCCRP-KLKCSKLFKLCNFSSA (SEQ ID NO:5).

GsMTx4 is available commercially and can also be isolated from spider venom by serial fractionation using standard chromatographic techniques. Its sequence is also disclosed in U.S. Pat. No. 7,125,847 (incorporated herein by reference). For example, fractionation of the spider venom is carried out using reverse phase high performance liquid chromatography (HPLC). Reverse phase HPLC can be performed using C-8 or C-18 silica columns and trifluoroacetic acid/acetonitrile buffer system. C-8 and C-18 silica columns are commercially available (Mac-Mod Analytical, Inc., West Chester, Pa.).

The peptide GsMTx4 and its variants can also be prepared by chemical synthesis using automated or manual solid phase methods. Such technologies are well known in the art. For example, such technologies are described in E. Atherton and R. C. Sheppard, Solid Phase Peptide Synthesis: A Practical Approach, IRL Press/Oxford University Press, Oxford, England, 1989; and M. Bodanzky, Peptide Chemistry: A Practical Textbook, Springer-Verlag, New York, N.Y., 1988. Thus, the peptide GsMTx-4 can be synthesized using Fmoc chemistry or an automated synthesizer. Depending upon quantitative yields, production of the linear reduced peptide can be performed in either a single process or in two different processes followed by a condensation reaction to join the fragments. A variety of protecting groups can be incorporated into the synthesis of linear peptide so as to facilitate isolation, purification and/or yield of the desired peptide. Protection of cysteine residues in the peptide can be accomplished using protective agents such as triphenylmethyl, acetamidomethyl and/or 4-methoxybenzyl group in any combination.

The peptide GsMTx4 and its variants may also be prepared by recombinant DNA technology. A DNA sequence coding for the peptide is prepared, inserted into an expression vector and expressed in an appropriate host cell. The expressed peptide can then be purified from the host cells and/or culture medium. Methods for preparing DNA coding for the peptide and expression of DNA are well known to those skilled in the art and are found for example, in Sambrook et al., (1989) Molecular Cloning: A Laboratory Manual, Cold Spring Harbor, N.Y., S. L. Berger and A. R. Kimmel, Eds., Guide to Molecular Cloning Techniques: Methods in Enzymology, vol 152, Academic Press, San Diego, Calif., 1987, and in E. J. Murray, Ed., Gene Transfer and Expression Protocols: Methods in Molecular Biology, vol 7, Humana Press, Clifton, N.J., 1991. In addition, the cloning of a cDNA encoding the GsMTx4 peptide is also disclosed.

Each peptide described herein for use in the compositions and methods of the invention can comprise or consist of the amino acid sequence provided for it. The peptides presented herein may have an N-terminal amide. In one embodiment, the present invention provides pharmaceutical compositions comprising a peptide which is 34, 35 or 36 amino acids long and comprises the sequence of SEQ ID No. 2. In another embodiment, the pharmaceutical composition comprises a peptide which is 34, 35 or 36 amino acids long and comprises the sequence of SEQ ID NO:1. In another embodiment, the pharmaceutical composition comprises a peptide which is 34, 35, 36 amino acids long and comprises the sequence of SEQ ID NO:3, 4 or 5. The amount of GsMTx4 or its variants in the pharmaceutical composition can be determined by empirical methods. Those skilled in the art will recognize that the dosage administered to a particular individual will depend on a number of factors such as the route of administration, the duration of treatment, the size and physical condition of the individual, and the patient's response to the peptide. The lack of any measurable toxicity of GsMTx4 in animal studies provides flexibility for designing a broad range of dosage regimens. For example, there was no toxicity observed in month long tests in mice using 5 mg/kg subcutaneous daily dose. The dosage regimen can include daily administrations, weekly or other suitable administrations. Extended release mechanisms can also be used. The term "treatment" as used herein means reducing the severity of one or more symptoms of or associated with sickle cell anemia.

Figure 9A:
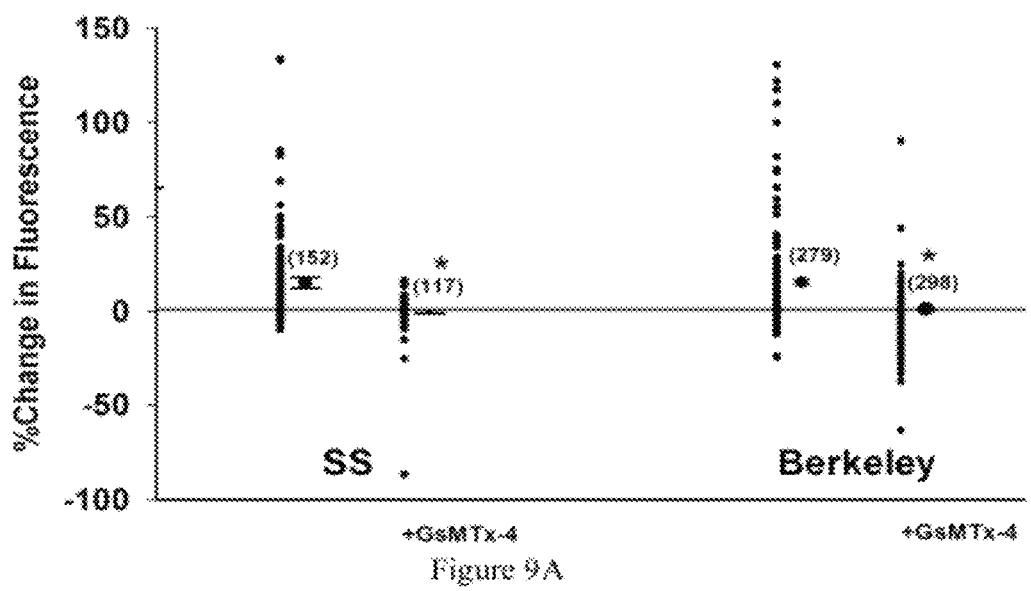
FIG. 9A. Changes in Fluo-3 fluorescence intensity in (n) individual human SS red cells 210 sec after deoxygenation (*, P<10-9), and in (n) individual Berkeley sickle mouse red cells 300 sec after deoxygenation (*, P<10-7). 1 µM GsMTx-4 was absent or present as indicated. B. Change in Fluo-3 fluorescence intensity in (n) individual SAD sickle mouse red cells 100 sec after deoxygenation, in the absence and presence of 1 µM GsMTx-4 (P<10-9). The selected time points are those of maximally elevated mean [Ca2+]i as observed in FIG. 2 for SAD mouse cells, in FIG. 3 for Berkeley mouse cells, and in FIG. 4 for human SS cells.
Figure 9B:
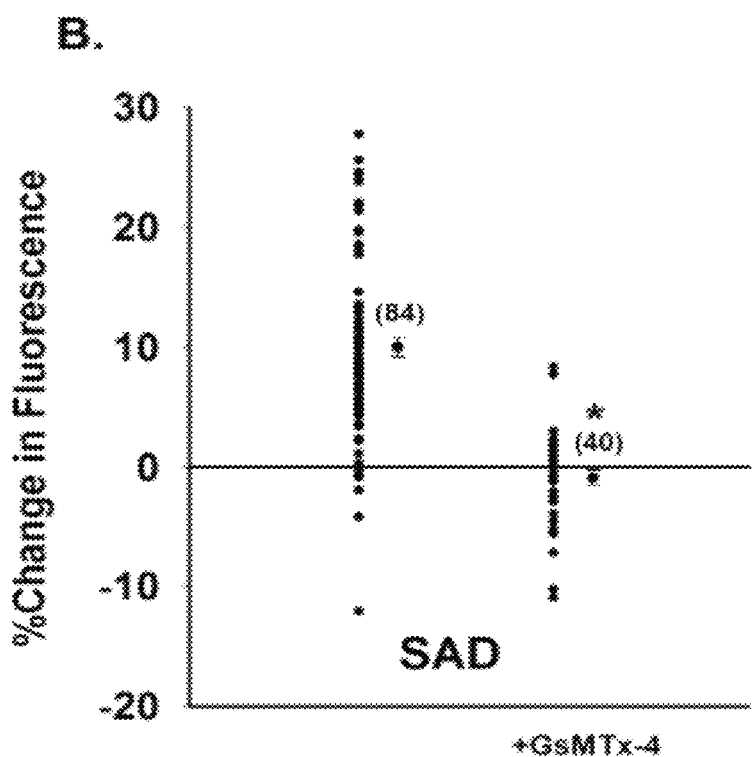

The peptide GsMTx4 of the present invention can be prepared for pharmaceutical use by incorporation with a pharmaceutically acceptable carrier or diluent. The peptide can be formulated into tablets, capsules, caplets and the like. Suitable carriers for tablets include calcium carbonate, starch, lactose, talc, magnesium stearate and gum *acacia*. The peptide can also be formulated for oral, parenteral or intravenous administration in aqueous solutions, aqueous alcohol, glycol or oil solutions or emulsions. The peptide can also be formulated for inhaling by encapsulating to facilitate alveolar absorption as has been done for insulin (Inhale Therapeutic Systems, San Carlos, Calif., inhale.com). Pharmaceutical compositions suitable for such routes of administration are well known in the art. For example, suitable forms and compositions of pharmaceutical preparations can be found in Remington's Pharmaceutical Science, 1980, 15.sup.thed. Mack Publishing Co., Easton, Pa. Thus, the peptide GsMTx4 can be administered orally, subcutaneously, parenterally, intravenously, intramuscularly or intranasally. The peptide may also be applied to medical devices that will come into contact blood. Both L and D enantiomers of GsMTx4's and its variants can be used for the present invention. We have previously shown that both L- and D-GsMTx4 block mechanosensitive channel (MSC) activity. Although, we have noted differences in the effects of these enantiomers, both forms are effective. For example, we have observed that the ability of the mirror image form (D-enantiomer) to inhibit mechanically activated ion channels is similar to the wild type peptide (L-form) (Suchyna et al 2004). Additionally, data presented here (FIG. 9) shows that the D-form did not stimulate neurite initiation as did the L-form, but no significant effect was observed on neurite length with either the L or D form. Thus, both L and the D forms can be used in the present invention.

In addition to use for sickle cell anemia, other uses of L and/or D forms of GsMTx4 include muscular dystrophy, atrial fibrillation, pain, incontinence, Parkinson's disease, nerve regeneration, glioma and other cancers, brain and cardiac damage from pressure overload caused by explosives, other degenerative muscle disease that whose pathology involves overstressing mechanosensitive channels use as antibiotics, use in heart (or other) transplants, use for relieving cardiac stress in acute cardiac stress, Alzheimer's disease, and diseases the involve mechanosensitive ion channels.

The present peptide, GsMTx4 and/or its variants can be used in combination with other therapeutic approaches to treat sickle cell anemia.

The following Examples are meant to illustrate, but not limit the invention

Example 1

Materials and Methods

Grammastola spatulata mechanotoxin 4 (GsMTx4) was purified according to Suchyna et al. 2000) from G. spatulata crude venom (Spider Pharm, Yarnell, 5 AZ) or purchased from Peptide International (Louisville, Ky.). 4,4'-diisothiocyanatostilbene-2,2'-disulfonic acid (DIDS) was from Calbiochem (San Diego, Calif.). Other drugs and analytical grade salts were from Sigma or Fluka (St. Louis, Mo.). In some experiments, the peptide GsMTx4 was prepared by solid state chemical synthesis.

Blood cell preparation: Human SS and AA blood was obtained under IRB-approved protocols of Children's Hospital and Beth Israel Deaconess Medical Center. After buffy coat removal and 5 washes in standard human red cell wash solution containing (in mM) 150 choline Cl, 1 MgCl, and 10 Tris-MOPS, pH 7.4, red cells were resuspended in storage solution containing (in mM) 145 KCl, 15 NaCl, and 10 HEPES, pH 7.4, then kept at 4° C. until used. Human red cells allowed to settle on coverslips were mounted on an inverted microscope in a 200 µl open chamber (WPI, Sarasota, Fla.) and superfused 15 min at room temperature by bath solution containing (in mM) 150 Na methanesulfonate, 10 Na EDTA, and 10 Na HEPES, pH 7.4.

Blood was withdrawn by cardiac puncture or from the tail vein of C57Bl6/J wildtype mice, SAD sickle mice, or Berkeley sickle mice into heparinized syringes by IACUC-approved protocols of Beth Israel Deaconess Medical Center. Buffy coat-depleted cells were washed 5 times in standard mouse red cell wash solution containing (in mM) 172 choline Cl, 10 sucrose, 10 Na Tris-MOPS, pH 7.4, resuspended in storage solution, and kept at 4° C. until use.

Mouse red cells allowed to settle on coverslips were superfused 15 min with bath solution containing (in mM) either 150 mM Na methanesulfonate, 10 Na EDTA, and 10 Na HEPES, pH 7.4; or 140 NaCl, 4 KCl, 1CaCl$_2$, 1 MgCl$_2$, 10 Na HEPES, pH 7.4. Deoxygenation was achieved by switching superfusate to the same solution gassed ≥30 min prior to the experiment with 100% N$_2$, and by flushing of the perfusion chamber with N2 during the deoxygenation period. The resulting bath pO$_2$ was 18 mm Hg as measured by oxygen electrode (WPI). In the experiments of FIG. 1, deoxygenated cells were subsequently re-oxygenated by exposure to the same superfusate equilibrated with room air.

Washed human or mouse red cells in solution containing (in mM) 140 NaCl, 5 KCl, 1 CaCl$_2$, 1 MgCl$_2$, 10 Na HEPES, pH 7.4 were exposed for 1 hr on a rotary platform in a 37° C. incubator to 25 ppm carbon monoxide (CO) in 5% CO$_2$. CO-exposed cells were then subjected to patch clamp or to calcium imaging experiments within 60 min after return to room air, using the solutions indicated.

On-cell patch clamp: Borosilicate pipettes (Corning 7052) pulled with a Narishige two stage puller or a Sutter P97 puller and fire-polished to resistances of 10-20 MΩ were front-filled and then backfilled. Symmetric bath and pipette solutions for studies of seal resistance stability during reversibility tests of the deoxygenation-activated conductance in SAD mouse red cells were (in mM) 140 NaCl, 4 KCl, 1 CaCl$_2$, 1 MgCl$_2$, 10 Na HEPES, pH 7.4. These conditions yielded tight seals in 13% of patch attempts on SAD cells. For study of deoxygenation-induced monovalent cation permeation in the absence of bath Ca$^{2+}$ and Mg$^{2+}$ recorded in SAD and Berkeley mouse cells and in human cells, symmetric bath and pipette solutions contained (in mM) 150 Na methanesulfonate, 10 Na EDTA, and 10 Na HEPES, pH 7.4. These conditions yielded tight seals in 16% of patch attempts on SAD mouse red cells, 26% of attempts on Berkeley mouse cells, and 30% of attempts on human SS cells. For study of Ca$^{2+}$ permeation in human SS cells, bath and pipette solutions contained (in mM) 100 CaCl$_2$, 10 Na HEPES, pH 7.4. These conditions yielded tights seals on 44% of attempts. For all conditions tested in human red cells, 70% of tight seals were sustained through the solution change accompanying deoxygenation to allow recording of current activity.

On-cell patch currents were recorded with the Axopatch 1-D amplifier (Axon Instruments/Molecular Devices, Sunnyvale, Calif.). Holding potential was −Vp=−50 mV (expressed as the negative of the pipette potential (e.g., equivalent to the intracellular potential with respect to the pipette). To determine current-voltage relationships (I-V curves) in Fetchex or Clampex (PCLAMP, Axon Instruments), the realtime control window in gap-free mode was used to record current traces of 10-30 sec duration at holding potentials ranging from −100 to +100 mV, in 25 mV increments. The bath reference electrode was a silver chloride wire with a 3 M KCl agar bridge. Data was filtered at 500 Hz, digitized at 2 kHz by Clampex, and analyzed offline by Fetchan and Pstat or by Clampfit subroutines of PCLAMP. Holding potentials in on-cell patch experiments were expressed as −Vp, the negative of the pipette potential.

Nystatin-permeabilized on-cell patch conditions were modified from Mahaut-Smith as previously described (Mahaut-Smith 1995, Physiol., 484(pt 1):15-24; Alper et al. 2008), using symmetric bath and pipette solutions of 150 mM Na methanesulfonate. These nominal whole cell currents were recorded with the Axopatch 1-D amplifier, and normalized to capacitance as measured by analysis of the current transient elicited by stepping to +100 mV. I-V curves were measured during sequential 20 mV voltage steps of 200 msec clamp duration, between −100 mV and +80 mV. Output was digitized, filtered, and analyzed offline as above.

Fluorescence measurements of cytosolic [Ca$^{2+}$] ([Ca$^{2+}$]$_i$): After removal of plasma and buffy coat by aspiration, human or mouse red cells were washed three times at room temperature and suspended in modified Hank's solution containing (in mM), 137 NaCl, 5.4 KCl, 1 CaCl$_2$, 1 MgCl$_2$, 0.8 NaK phosphate, 5.6 glucose, and 10 Na HEPES, pH 7.4. Dilute cell suspensions were settled on polylysine-coated coverslips forming the bottom of an open perfusion chamber (2.5 cm diameter, 1 cm depth) and washed again 3 times.

Measurement of relative changes in [Ca$^{2+}$]$_i$ by Fluo-3 fluorescence emission was previously validated in intact human (Yang et al. 2000, Blood, 95(7):2421-2425; Andrews et al. 2002, Blood, 199(9):3392-3399) and mouse red cells (Akel et al. 2007, Amer. J. Physiol., 292(5):C1759-1767). Attached red cells were loaded in the dark with the fluorescent non-ratiometric Ca$^{2+}$ indicator Fluo-3-AM (10 µM, Molecular Probes, Eugene, Oreg.) at 37° C. for 1 hr, then washed and incubated 15 min further to allow de-esterification of intracellular dye. The open perfusion chamber containing dye-loaded cells was mounted on an Olympus IMT-2 inverted epifluorescence microscope equipped with CoolSNAP CCD camera (Photometrics, Tucson, Ariz.). Fluo-3 in cells imaged through a 60× objective was excited by mercury-xenon illumination passed through a 495ds20 filter. Fluorescence emission (proportional to $[Ca^{2+}]_i$) from a 535ds20 bandpass filter was collected from all attached single cells within the arbitrarily selected visual field. Emission image acquisition was controlled by a Metafluor digital imaging system (Universal Imaging, West Chester, Pa.).

Fluo-3 fluorescence from attached cells on each coverslip was recorded 60 sec in room air and then for 10 min after onset of perfusion chamber flushing with humidified 100% N2. The normalized increase in Fluo-3 fluorescence in SS cells subjected to this deoxygenation procedure was indistinguishable from that observed during superfusion of cells in a closed perfusion chamber via syringe pump with bath previously bubbled for 60 min with 100% $N_2$ (n=62 cells from 2 SS patients, not shown). The y-axis value of 0% change in Fluo-3 fluorescence intensity represented mean intensity recorded from all cells within the coverslip visual field during the 60 sec prior to deoxygenation.

Total red cell exposure time to acetoxymethyl ester from the start of Fluo-3-AM loading to the end of our fluorescence measurements was 90 min. ATP concentrations in human red cells incubated for 4 hrs under similar conditions, in the presence of glucose without pyruvate supplementation, were shown previously not to fall below 80% of initial values (Yang et al. 2000).

Mouse breeding: C57BL6/J inbred mice and Berkeley sickle mice ($Hba^{tm1Paz}Hbb^{tm1/Tow}$ Tg(HBA-HBBs)41Paz/J) purchased from JAX (Bar Harbor, Me.) were bred and genotyped as recommended by JAX protocol (jaxmice.jax.org/strain/003342). SAD-1 sickle mice ($Hbb^{S/S}$ Tg(HBAHBB-SAD-1) transgenic for one copy of the hypersickling human β-globin gene carrying the three mutations βS $^6$Val, β S-Antilles $^{23}$Ile, and β D Punjab $^{121}$Gln and (in the founder expressed in their red cells ~19% Hb SAD ($a2^{human}\beta2^{SAD}$), mouse Hb, and mouse-human hybrid Hb (Trudel et al. 1991, The EMBO J. 10(11):3157-3165; De Franceschi et al. 1994, J. Clin. Invest., 93(4):1670-1676; Rust et al. 2007, J. Clin Invest., 117(6):1708-1717) (SAD mice), were crossed with Kcnn4−/−mice (Begenisich et al. 2004) ultimately to generate Kcnn4−/−progeny carrying the SAD transgene. SAD× Kcnn4−/−progeny were born at Mendelian ratios, and exhibited no gross phenotypic difference from SAD mice. KCa3.1 genotyping (Begenisich et al. 2004) and Hb β-SAD genotyping protocols (Rust et al. 2007) were as described.

Statistical analysis: Statistical analyses were performed with SigmaStat v.2.03 (SSPS, Chicago, Ill.). Paired or unpaired t-tests, the Mann-Whitney test, or the Wilcoxon rank-order test were used as indicated.

Results

Figure 1B:
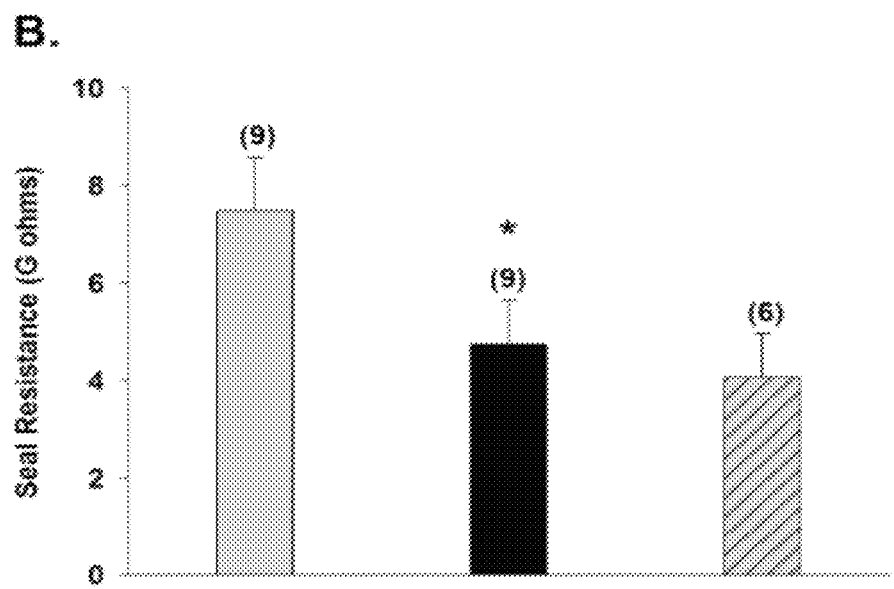
Figure 1C:
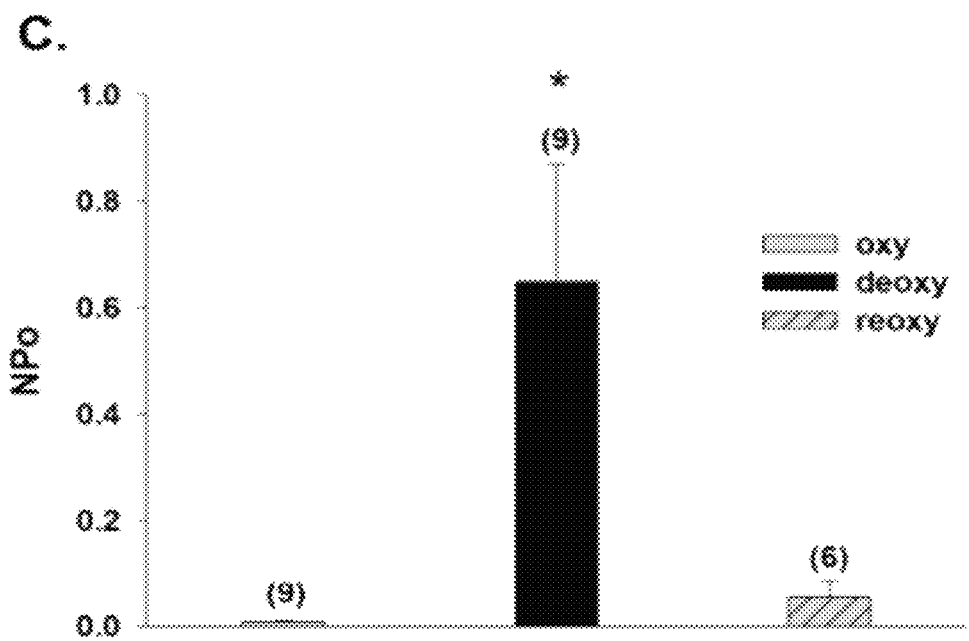

The on-cell patch records of FIG. 1A, with NaCl in both pipette and bath, show that deoxygenation activates noisy channel activity in the SAD sickle mouse red cell membrane. Deoxygenation increased SAD red cell patch NPo from the room air value of 0.01±0.01 to 0.65±0.22 (n=9). Subsequent reoxygenation decreased nPo to 0.06±0.03 in those patches that survived (n=6; FIG. 1C). Calculated chord conductance was 20 pS (between −Vp=0 and −50 mV; n=9). Visual inspection of current traces indicated onset of increased activity at 7.5±3.1 sec after deoxygenation (n=9; measured from the bath solution change artifact). The nearly complete cessation of channel activity upon re-oxygenation was accompanied by maintenance of a stable giga-ohm seal (FIG. 1B). The time to steady-state recovery of quiescence after reoxygenation was 57±20 sec (n=6). Thus, the noisy nature of the deoxygenation-induced conductance in on-cell patches did not reflect deoxygenation-induced leak due to loss of the original tight seal.

Figure 2A:
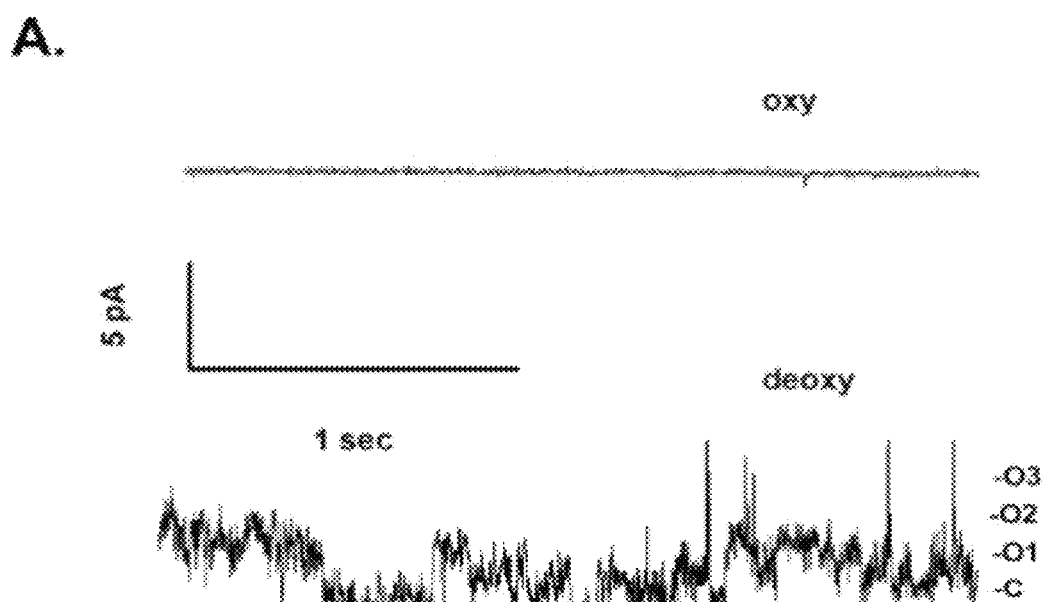
FIG. 2. Deoxygenation activates conductance and increases [Ca2+]i in red cells from SAD sickle mice A. Representative current trace from an individual cell-attached patch on a SAD mouse erythrocyte, recorded first in oxygenated (upper trace, oxy, $-V_p=-25$ mV) and subsequently in deoxygenated conditions (lower trace, deoxy, $-V_p=+75$ mV). Symmetrical pipette and bath solutions contained (in mM) 150 Na methanesulfonate, 10 Na ethylenediaminetetraacetic acid (EDTA), and 10 Na HEPES, pH 7.4. B. Deoxygenation increased the NPo of 6 cell-attached patches recorded in symmetrical Na methanesulfate (*, p<0.05; n=6). Substitution of pipette solution Na+ with NMDG blocked the deoxygenation-induced increase in NPo (n=5). Values are means+s.e.m, recorded at $-V_p=-25$ mV. C. Current-voltage relationship in a representative cell-attached patch on a SAD red cell exposed to deoxygenation with symmetrical Na methanesulfonate solutions in pipette and bath. Mean+s.e.m. for fit of the amplitude histogram. D. Deoxygenation increases [Ca2+]i in SAD red cells but not in WT mouse red cells, in a manner inhibited by 1 µM GsMTx-4 and enhanced by 50 µM vanadate. Values are means+s.e.m. of Fluo-3 fluorescence increase for (n) red cells from 3 mice studied in 8 experiments (SAD), from 1 mouse studied in 4 experiments (WT and SAD+GsMTx-4) or from 1 mouse studied in 2 experiments (SAD+vanadate).
Figure 2B:
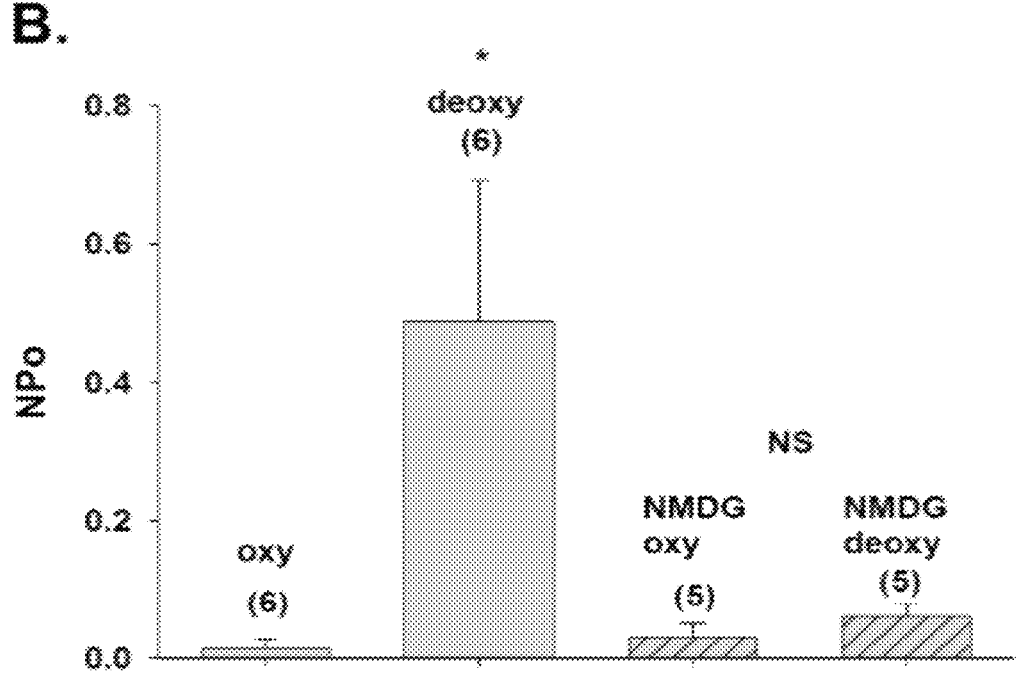
Figure 2C:
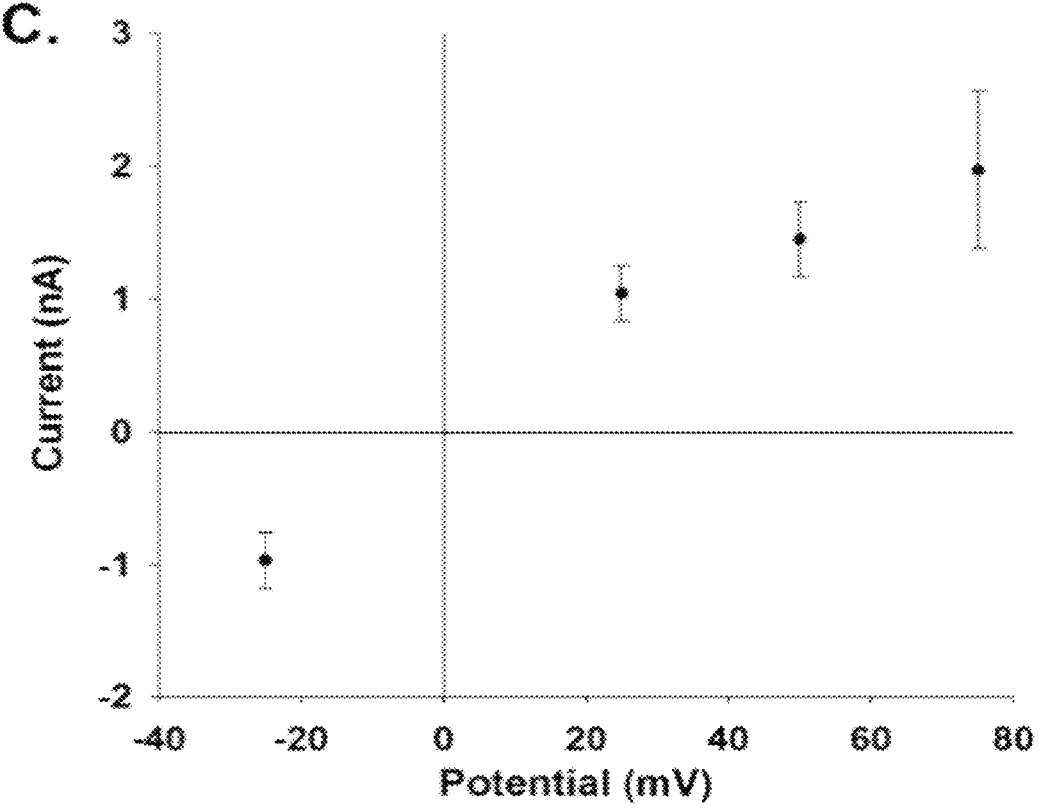

Deoxygenation of SAD sickle mouse red cells increases cation conductance and elevates $[Ca^{2+}]_i$: To minimize the contribution of anion currents to measured currents, and to enhance detection of monovalent cation currents, the effects of deoxygenation in SAD cells were studied in a Na methanesulfonate bath free of $Ca^{2+}$. The pipette also contained Na methanesulfonate. The representative on-cell patch shown in FIG. 2A was quiescent in room air, but upon deoxygenation exhibited channel activity with a chord conductance of 27 pS (between −Vp=+25 and −25 mV) and reversal potential (Erev) of +1 mV (FIG. 2C). As shown in FIG. 2B, deoxygenation increased mean NPo in SAD mouse red cell patches from 0.01±0.013 to 0.48±0.20 (n=6; p<0.05). Patch duration under deoxygenation in these experiments was 8.4±1.8 min. Estimated single channel amplitude at −Vp=25 mV was 0.70±0.14 pA (n=6), with a calculated inward chord conductance of 28 pS (0 to −25 pS). With NMDG chloride rather than Na methanesulfonate in the pipette, room air patch NPo of 0.03 was unchanged by deoxygenation at 0.06 (n=5, P=0.28). The data demonstrate the activation by deoxygenation of nonspecific cation channel activity in the SAD mouse red cell membrane.

Figure 2D:
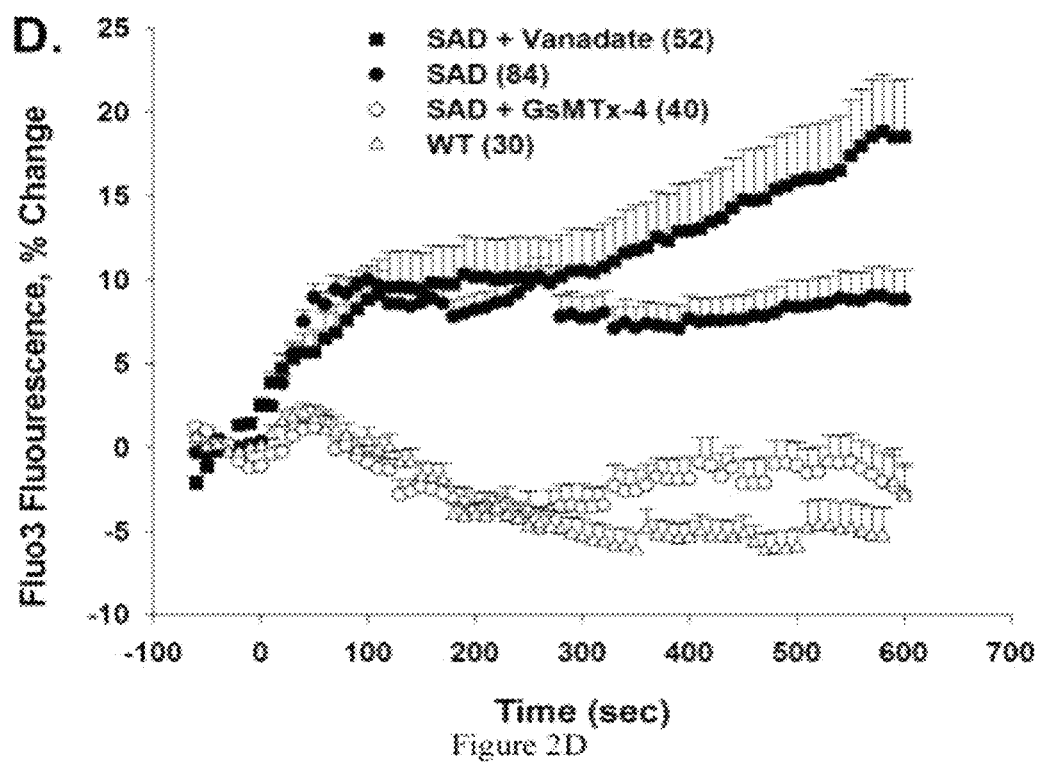

Since the proximate pathological consequence of Psickle activation is believed to be elevation of SS cell $[Ca^{2+}]_i$, we monitored Fluo-3 fluorescence emission during deoxygenation in SAD cells. Deoxygenation was found to increase $[Ca^{2+}]_i$ in SAD red cells (P<10$^{-5}$) but not in red cells from the parental strain C57B16/J (FIG. 2D). The increased $[Ca^{2+}]_i$ accompanying deoxygenation was completely inhibited by a blocker of stretch-activated ion channels, GsMTx-4 (1 μM, P<10$^{-5}$). The role of red cell plasma membrane Ca2$^+$-ATPase (PMCA) in controlling the maximal value of $[Ca^{2+}]_i$ induced by deoxygenation was tested by bath addition of 50 μM Na vanadate (FIG. 2D), a concentration sufficient for near-complete inhibition of human red cell plasma membrane calcium ATPase (PMCA). During 5 min normoxic vanadate preincubation of SAD cells, $[Ca^{2+}]_i$-dependent Fluo-3 emission increased 12.8±1.8%. Acute deoxygenation in the continued presence of vanadate further elevated SAD red cell $[Ca^{2+}]_i$, with kinetics similar to those in the absence of vanadate, achieving plateau values within <2 min. However, after ~4 min longer at this plateau value, vanadate-exposed cell $[Ca^{2+}]_i$ slowly increased to twice the previous plateau value (FIG. 2D). This late elevation might reflect PMCA inhibition by ATP depletion (the bath solution lacks pyruvate or glucose), or recruitment of the distinct, vanadate-induced $Ca^{2+}$ entry pathway.

Figure 3A:
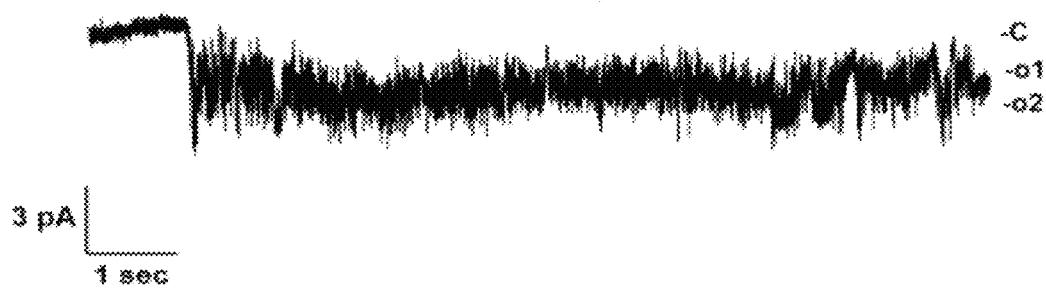
FIG. 3. Deoxygenation activates conductance and increases [Ca2+]i in red cells from Berkeley sickle mice. A. Representative current trace from an individual cell-attached patch on a Berkeley sickle mouse erythrocyte. Symmetrical pipette and bath solutions contained (in mM) 150 Na methanesulfonate, 10 Na EDTA, and 10 Na HEPES, pH 7.4. The cell was subjected to deoxygenation at t=0. $-V_p=-25$ mV. B. Deoxygenation increased in Berkeley mouse cells (n=4), but not in C57BL6/J cells (n=3). Values are means+s.e.m, recorded at $-V_p=-25$ mV. C. Current-voltage relationship of channel activity activated by deoxygenation in Berkeley red cells. Mean+s.e.m. for fit of the amplitude histogram. D. Deoxygenation-increased [Ca2+]i in Berkeley red cells (9 experiments) was prevented by preincubation with 1 µM GsMtx-4 bath preincubation (7 experiments). Values are means+s.e.m. of Fluo-3 fluorescence increase for (n) red cells from 3 mice.
Figure 3B:
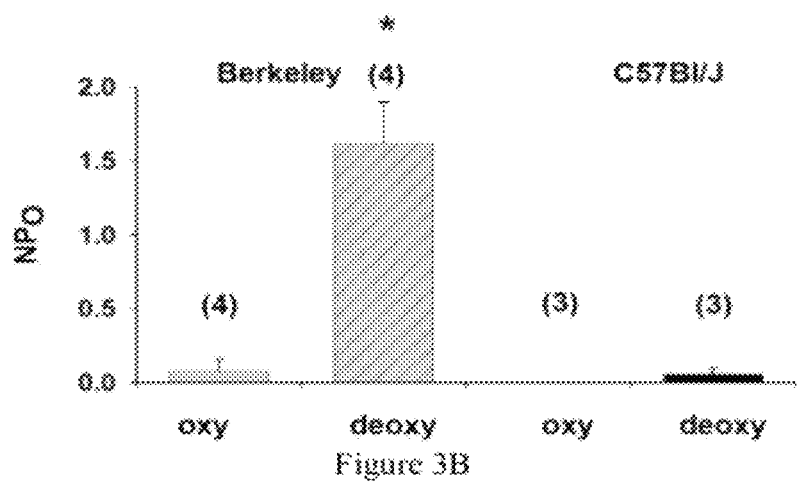
Figure 3C:
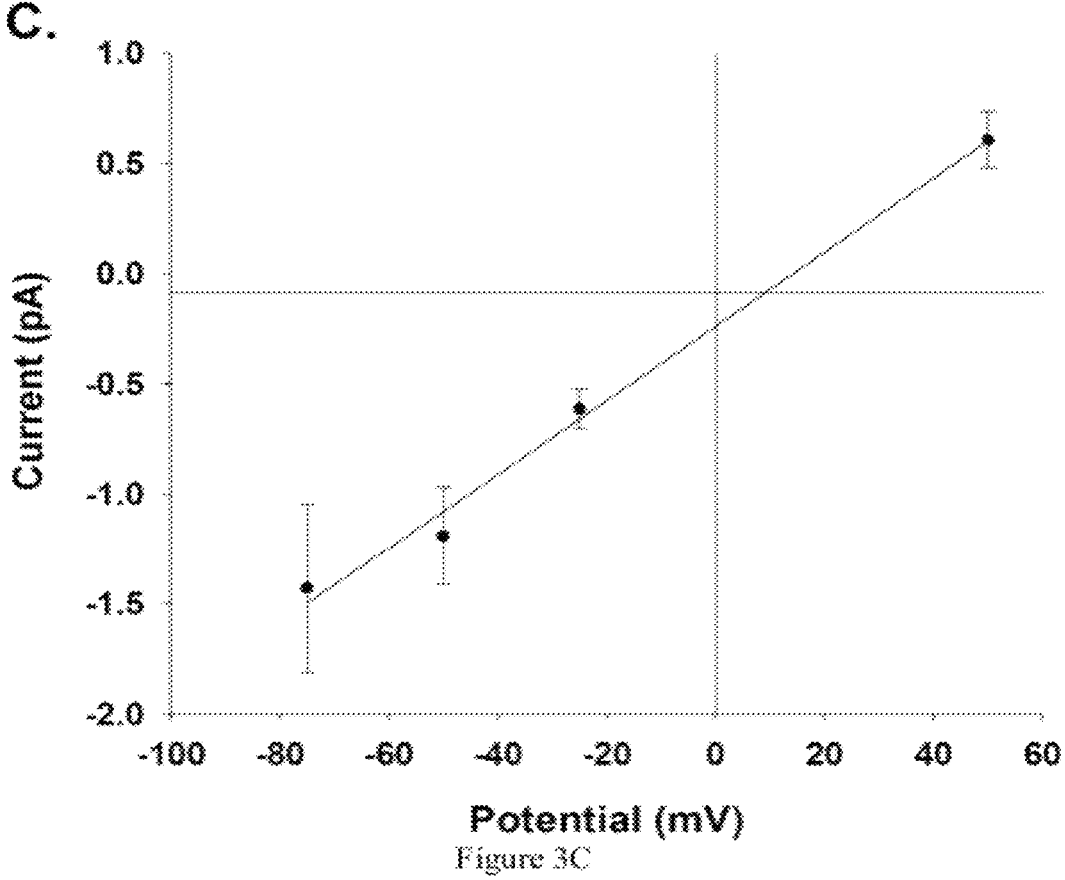
Figure 3D:
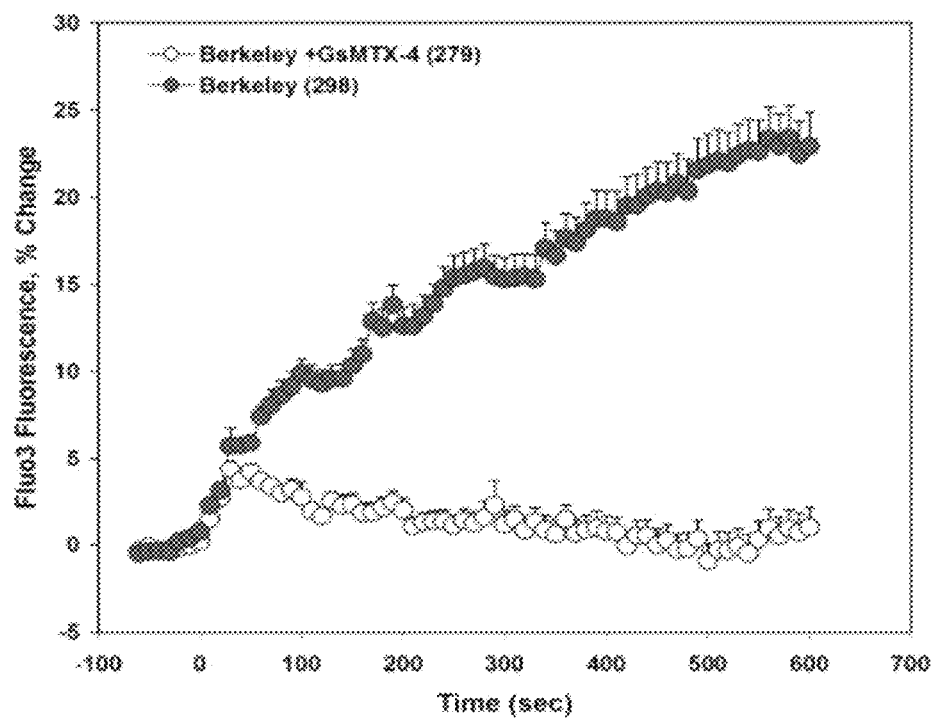

Deoxygenation of Berkeley sickle mouse red cells increases cation conductance and elevates $[Ca^{2+}]_i$: The Berkeley sickle mouse exhibits severe hemolytic anemia resembling humans with sickle-β-thalassemic disease. FIG. 3A shows a representative current trace from a cell-attached patch on a Berkeley mouse erythrocyte subjected to deoxygenation. Total seal duration in this individual experiment was 6.5 min, including 2 min in room air. Conductance was abruptly activated by deoxygenation after 1.1 sec in this experiment. However, the mean deoxygenation time prior to activation of conductance was 18±11 sec (n=5). Deoxygenation increased NPo from 0.081±0.080 to 1.62±0.28 in Berkeley sickle red cells (n=4, p<0.01), whereas NPo of oxygenated C57B16/J red cells (0.001±0.001) was only minimally increased by deoxygenation (0.057±0.038; n=3, FIG. 3B). Estimated single channel amplitude of deoxygenation-induced channels with Na methanesulfonate in pipette and bath was 0.62±0.06 pA at $-V_p=-25$ mV. Slope conductance in this patch (between $-V_p=-75$ and +50 mV) was 17 pS conductance with a reversal potential of +12 mV (FIG. 3C). Mean initial seal resistance of 1.8±0.2 GΩ in room air (n=5) was maintained under deoxygenated conditions, and just before loss of seal was 2.3±0.4 GΩ. Deoxygenation also increased Berkeley red cell $[Ca^{2+}]_i$ ($P<10^{-5}$), and this $[Ca^{2+}]_i$ elevation was inhibited nearly completely by 1 μM GsMTx-4 ($P<10^{-5}$; FIG. 3D).

Figure 4A:
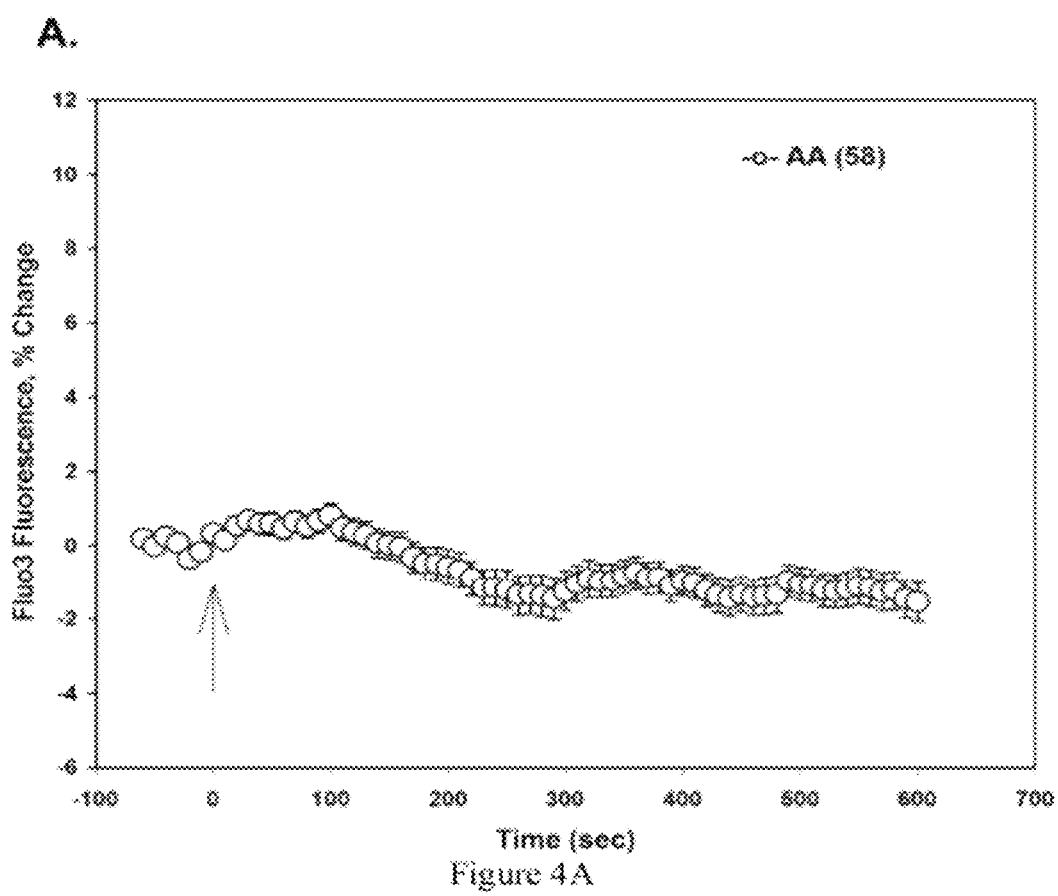
FIG. 4. Deoxygenation elevates [Ca2+]i in human SS red cells but not in human AA red cells. A. Fluo-3-loaded AA cells exposed to deoxygenation at t=0 (arrow) did not exhibit increased fluorescence, indicating lack of increase in [Ca2+]i. Values are means+s.e.m. from AA cells (n=58) from 2 subjects, as acquired during six experiments. B. Fluo-3-loaded human SS cells responded to deoxygenation with elevation of [Ca2+]i to peak, sustained values within 2-3 min (filled circles, SS cells (n=152) from 4 subjects, examined in 8 experiments). This increase was blocked by inclusion of 1 µM GsTMx-4 in the bath (open circles, SS cells (n=117) from 3 subjects, examined in 4 experiments) or by prior treatment with CO as described in Methods (open squares, SS cells (n=137) from 3 subjects, examined in 5 experiments). See FIG. 9 for fluorescence intensities of individual cells of each genotype at single time points of maximal [Ca2+]i elevation.
Figure 4B:
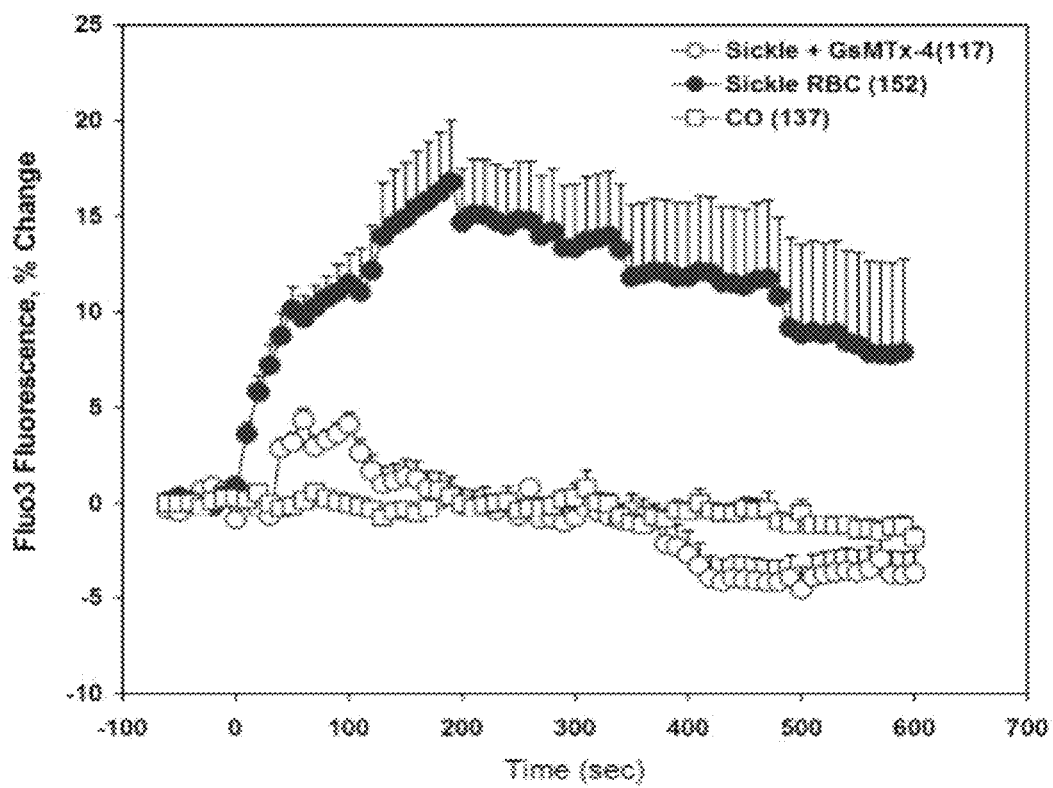

Deoxygenation increases $[Ca^{2+}]_i$ in SS cells: Deoxygenation of human sickle red cells has previously been noted to increase $^{45}Ca^{2+}$ influx. As shown in FIG. 4, deoxygenation also increased $[Ca^{2+}]_i$ in Fluo-3-loaded human SS red cells [($P<0.001$, Mann-Whitney test or unpaired two-tailed T test (FIG. 4B) but not in AA cells (FIG. 4A)]. The distribution of individual cell $[Ca^{2+}]_i$ values shows that not all SS cells responded to deoxygenation by elevating $[Ca^{2+}]_i$ (FIG. 9). 10 min pretreatment of SS cells with 1 μM GsMTx-4 prevented $[Ca^{2+}]_i$ elevation by subsequent deoxygenation in continued presence of the toxin ($P<0.001$, FIG. 4B). 30 min preincubation with CO also inhibited $[Ca^{2+}]_i$ elevation by deoxygenation (in the absence of continued CO exposure) ($P<0.001$, FIG. 4B). These results suggested that deoxygenation-activated elevation of $[Ca^{2+}]_I$ in SS cells required both HbS polymerization and activation of a (pharmacologically defined) stretch-activated ion conductance. The magnitude of the deoxygenation-induced increase in SS cell $[Ca^{2+}]_i$ was considerably lower than elicited in SS cells by 5 μM LPA (FIG. 10C).

Figure 5A:
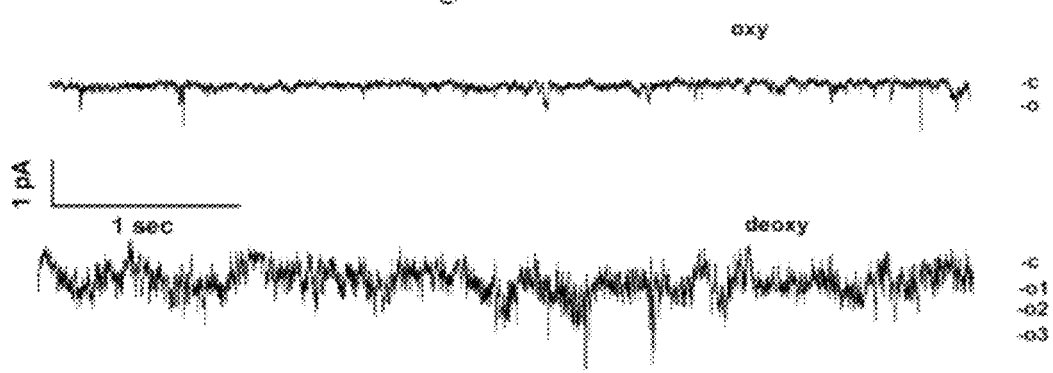
FIG. 5. Deoxygenation activates a Ca2+-permeable conductance in human SS cells. A. Representative current traces from a cell-attached patch on an individual human SS erythrocyte recorded before (oxy) and after onset of deoxygenation (deoxy). Pipette solution contained (in mM) 100 CaCl2, 10 Na HEPES, pH 7.4. Bath solution contained (in mM) 150 Na methanesulfonate, 10 Na HEPES, pH 7.4. Holding potential was $-V_p=-25$ mV. Open states at right are derived from the open state histogram (not shown). B. Current-voltage relationship derived from the deoxygenated currents measured in the patch of panel A. Mean+s.e.m. for fit of amplitude histogram. C. The low NPo of inward single channel activity of human SS cells recorded in the on-cell configuration with Ca2+ in the pipet is increased by deoxygenation (*, p<0.02). The deoxygenation-induced increase in NPo is prevented by inclusion of 1 µM GsMTx-4 in the pipette. Values are means+s.e.m. (n=4-5), recorded at $-V_p=-25$ mV.
Figure 5B:
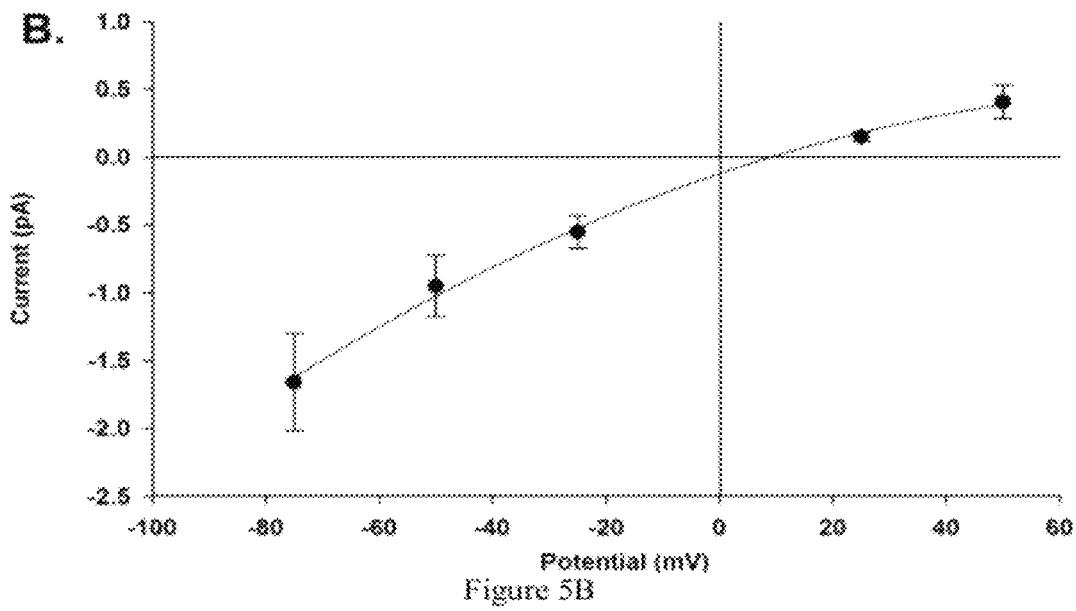
Figure 5C:
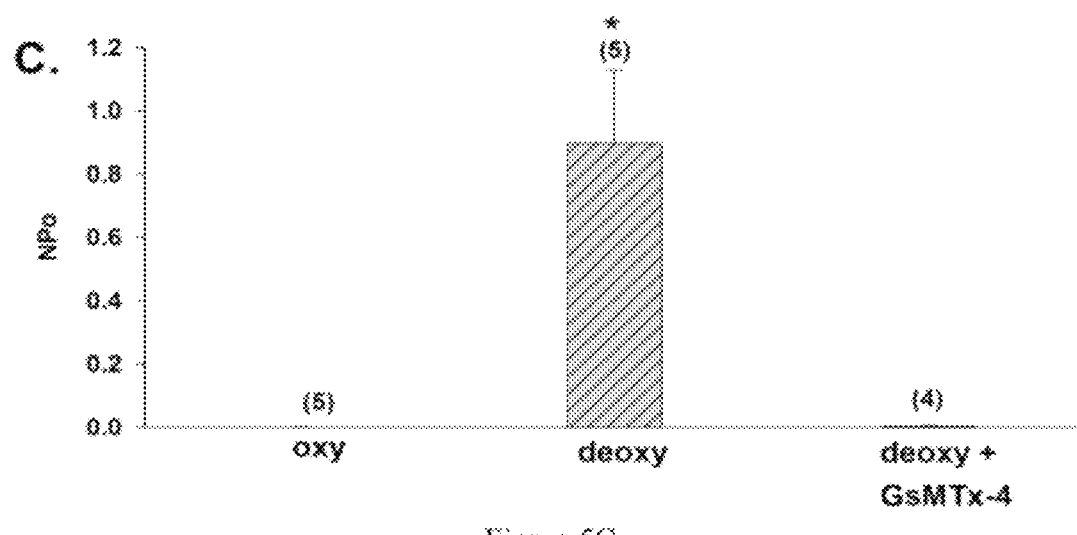

Deoxygenation activates a $Ca^{2+}$-permeable conductance in cell-attached patches of human SS cells: $Ca^{2+}$ entry into deoxygenated SS cells via Psickle is believed to be a major trigger of SS cell dehydration via KCa3.1. However, in the experiments of (Browning et al. 2007), deoxygenation did not increase whole cell currents recorded in human SS cells in symmetrical $Ca^{2+}$ solutions. We therefore sought electrophysiological evidence of deoxygenation-activated $Ca^{2+}$ permeation in cell-attached patches with CaCl2 in the pipette and Na methanesulfonate in the bath. As shown in FIGS. 5A and 5C, deoxygenation increased patch conductance. Patch NPo was not different from zero in room air, but increased to 0.90±0.23 upon deoxygenation ($P<0.05$; n=5). Mean deoxygenation time prior to activation of conductance was 21±10 sec. The induced current displayed moderate inward rectification in these conditions, with amplitude of 0.64±0.089 pA at $-V_p=-25$ mV (n=5), corresponding to a 25 pS chord conductance. The I-V curve of the FIG. 5A patch, with Erev of +7 mV (FIG. 5B) was consistent with an inward $Ca^{2+}$ current and a substantial fraction of outward $K^+$ current through a nonspecific cation conductance. The calculated $E_{rev}(Cl^-)$, $-18$ mV for ~100 mM $[Cl^-]_i$ and more negative values as $[Cl^-]_i$ falls with increasing time in the methanesulfonate bath, suggests that the contribution of $Cl^-$ permeability to the observed currents is a minor one.

The initial seal resistance of 4.8±1.4 GΩ was maintained during deoxygenation, and was recorded at 3.7±0.9 GΩ just before loss of seal. Mean patch duration was 5.3±1.1 min. Inclusion of 1 μM GsMtx-4 in the pipette prevented activation by deoxygenation (FIG. 5C). Thus, the deoxygenation activated cation permeation pathway of SS cells revealed in cell-attached patch configuration conducts $Ca^{2+}$.

Figure 6A:
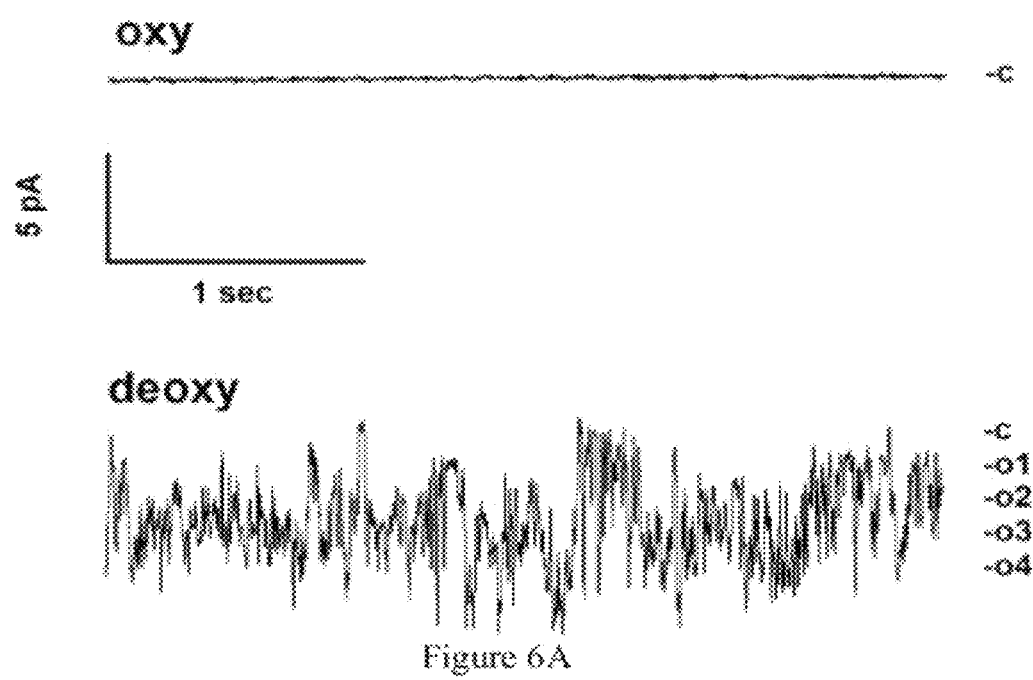
FIG. 6. Deoxygenation activates a cation-permeable conductance in human SS cells. A. Current traces recorded from an individual SS red cell patch of 4GΩ initial seal resistance before (upper trace, oxy) and 2 min after deoxygenation (lower trace, deoxy). Symmetrical pipette and bath solutions contained (in mM) 150 Na methanesulfonate, 10 Na EDTA, and 10 Na HEPES, pH 7.4. Holding potential was $-V_p=+50$ mV. Open states are at right. Tight seal recording continued under deoxygenated conditions for 8 min beyond the "deoxy" trace shown. Total patch duration was 14 min 18 sec. B. Amplitude histogram from 5 min recording in deoxygenated conditions showing the presence in the panel A patch of at least three equally spaced conductance levels of 1.2+0.3 pA magnitude (mean+s.d.), consistent with up to four channels in the patch. Estimates of the mean Gaussian fit in the histogram were made with the Simplex least squares method (pCLAMP). C. Dwell times of the first open state amplitude peak fit to a single exponential by the Simplex least squares method reveal τ=2 msec. D. Current-voltage relationship from the patch shown in panel A, with chord conductance of 29 pS. Mean+s.e.m. for fit of the amplitude histogram. E. NPo in AA red cells (leftmost two bars) and in SS red cells recorded at $-V_p=-50$ mV, first in room air and subsequently in deoxygenated conditions (leftmost 4 bars). NPo was measured in on-cell patches of additional SS cells before (not shown) and after deoxygenation in the presence of pipette solution containing GsMTx-4 (1 µM), dipyridamole (100 µM), or DIDS (100 µM), as indicated. Additional cells pretreated with CO prior to on-cell recording were recorded first in oxygenated and then subsequently in deoxygenated conditions (rightmost two bars). The drugs and the pretreatment with CO prevented deoxygenation-induced activation of conductance. Values are means+s.e.m. for (n) red cells.
Figure 6B:
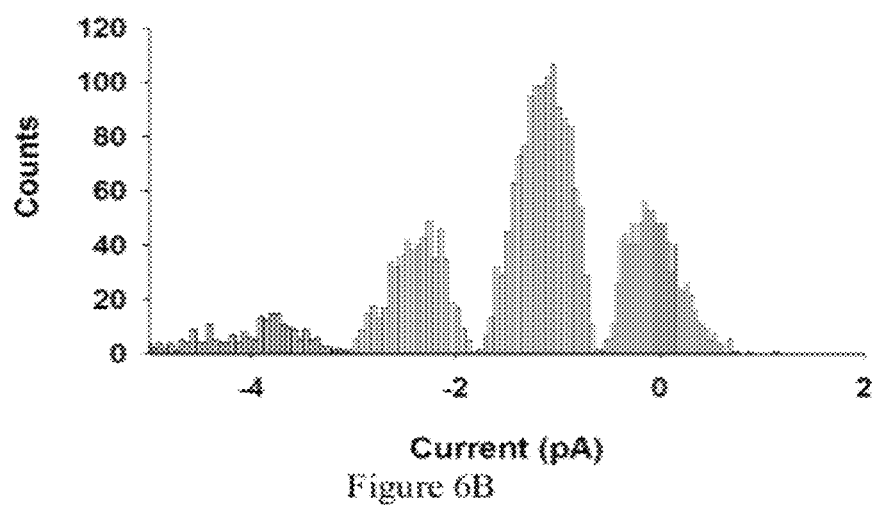
Figure 6C:
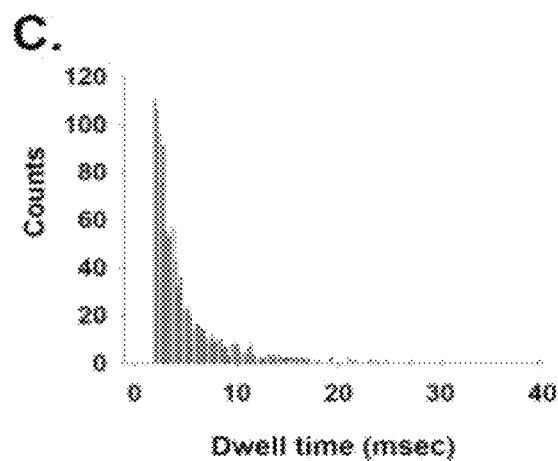
Figure 6D:
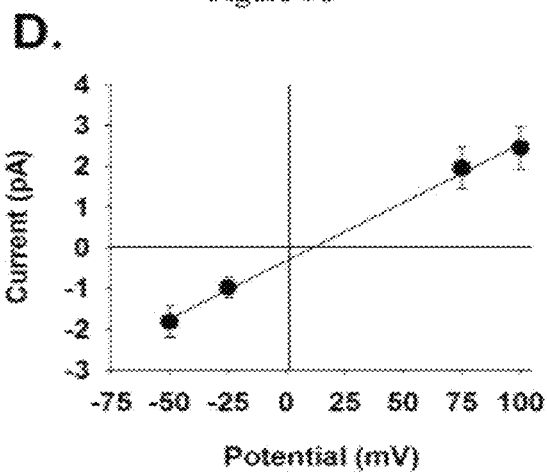
Figure 6E:
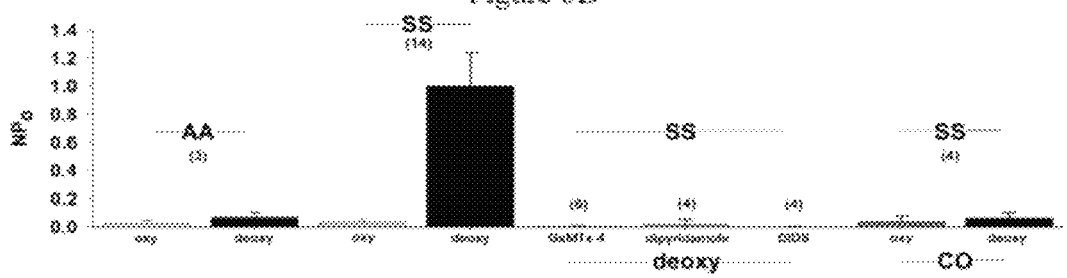

Deoxygenation activates a nonspecific cation conductance in cell-attached patches of human SS red cells: Psickle activated by deoxygenation has been characterized by nonspecific cation permeability. We therefore recorded deoxygenation-activated conductance in on-cell patches of SS cells with $Ca^{2+}$-free Na methanesulfonate in both pipette and bath. After switching the room-air equilibrated bath perfusate to perfusate equilibrated with and flushed with 100% $N_2$ (arrow), the initially quiescent patch shown in FIG. 6A exhibited within 5 seconds a gradually increasing noisy conductance activity that reached steady state within ~20 sec. In this representative patch, unitary currents of $-1.2\pm0.3$ pA (FIG. 6B) exhibited a dwell time of 2 msec (FIG. 6C) and a slope conductance of 29 pS (measured between $-V_p=-50$ and $=100$ mV) with reversal potential of +11 mV (FIG. 6D). The mean chord conductance from 14 similar deoxygenation experiments was 27±1 pS (measured between $-V_p=0$ and $-V_p=-50$ mV). Deoxygenation increased NPo at $-V_p=-50$ mV from 0.03±0.02 to 1.00±0.24 (n=14, P=0.002). This contrasted with AA cell-attached patches (FIG. 6E), in which deoxygenation increased NPo from 0.025±0.024 to 0.067±0.034 (n=3, P>0.05). All cells on which stable giga-ohm seals were established and maintained responded to deoxygenation with increased conductance. Mean on-cell patch seal duration in these conditions was 18±11 min. Initial seal resistance of 4.6±0.8 GΩ in room air was maintained under deoxygenated conditions at levels of 3.4±0.7 GΩ prior to seal loss.

The measured inward current could represent cellular $Cl^-$ efflux in addition to $Na^+$ influx from the pipette, but the near-zero reversal potential ($E_{rev}$) in the absence of pipette chloride strongly supported nonspecific cation-selectivity of this deoxygenation-activated current. The absence of inward current when the pipette contained NMDG chloride further supported the predominant contribution of cation conductance (n=3, not shown). These data and those of FIG. 5 are the first to document deoxygenation-activated conductance in on-cell patch records of individual human SS cells transitioning from room air to hypoxic conditions.

Pharmacological properties of deoxygenation-induced conductance activation in cell-attached patches of SS red cells: As was found for deoxygenation-activated $Ca^{2+}$ elevation, inclusion in the pipette of 1 μM GsMTx-4 prevented the deoxygenation-induced increase in cation conductance (NPo 0.003±0.003, n=6; FIG. 6D). GsMTx-4 treatment did not alter red cell shape (data not shown).

Inclusion of 100 μM dipyridamole in the patch pipette solution also prevented deoxygenation-induced activation of SS red cell membrane patch cation conductance. Normoxic NPo of 0.00 was unchanged at 0.004±0.002 after deoxygenation (n=4, P>0.05, not shown). Inclusion of 100 μM DIDS in the pipette similarly blocked conductance activation by deoxygenation, with respective normoxic and hypoxic NPo values of 0.002±0.002 and 0.001±0.001 (n=4, not shown). Dipyridamole and DIDS are nonspecific chloride channel blockers, but GsMTx-4 has not been previously reported to block anion channels. 1 μM GsMTx-4 had no effect on KCa3.1 activity stimulated in intact human AA cells by 1 μM A23187 in the presence of extracellular $Ca^{2+}$, measured as $^{86}Rb$ influx and as cell shrinkage (n=3 for each method, not shown). In contrast, A23187-stimulated $^{86}Rb^+$ influx has been reported to be completely inhibited by the highly specific KCa3.1 inhibitor charybdotoxin (50 nM) (Brugnara et al. 1993, J. Biol. Chem., 268(12): 8760-8768), and A23187-stimulated cell shrinkage was completely inhibited by the moderately specific KCa3.1 inhibitor, clotrimazole 10 μM; n=3, (data not shown; Brugnara et al. 1996, J. Clin. Invest., 97(5):1227-1234).

Figure 10A:
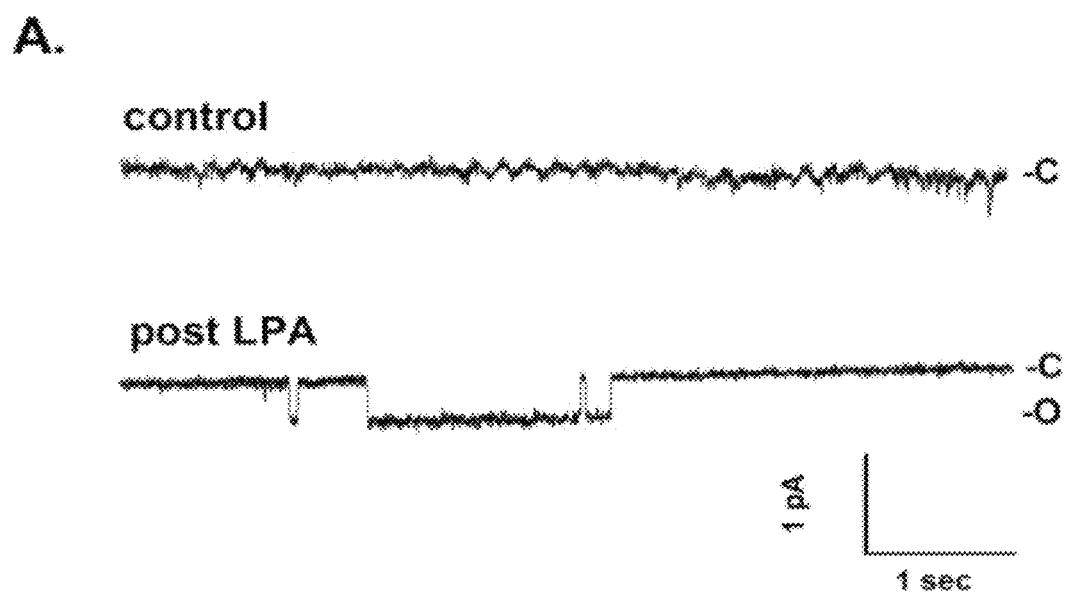
FIG. 10. Lysophosphatidic acid activates a cation-permeable channel in human SS red cells. A. On-cell patch recording from a human SS red cell before (upper trace) and after exposure to 5 µM lysophosphatidic acid (LPA, lower trace). Symmetrical bath and pipette solutions contained (in mM) 150 Na+ methanesulfonate, 10 Na EDTA, and 10 Na HEPES, pH 7.4. −Vp=−50 mV. B. LPA-induced increase in NPo was prevented by inclusion of either 1 µM GsMTx-4 or 100 µM dipyridamole in the pipette. Values are means+s.e.m. for 4-8 SS red cells; *, P<0.001. C. LPA elevated [Ca2+]i in human SS red cells, as indicated by Fluo-3 fluorescence increase. Values are means+s.e.m. for 75 SS red cells from 3 subjects examined in two experiments.
Figure 10B:
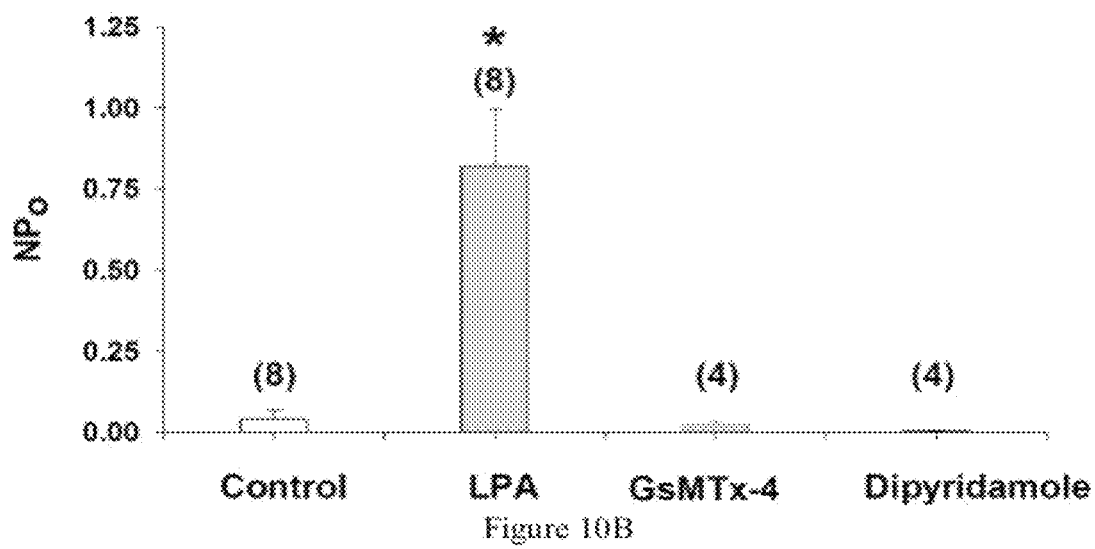
Figure 10C:
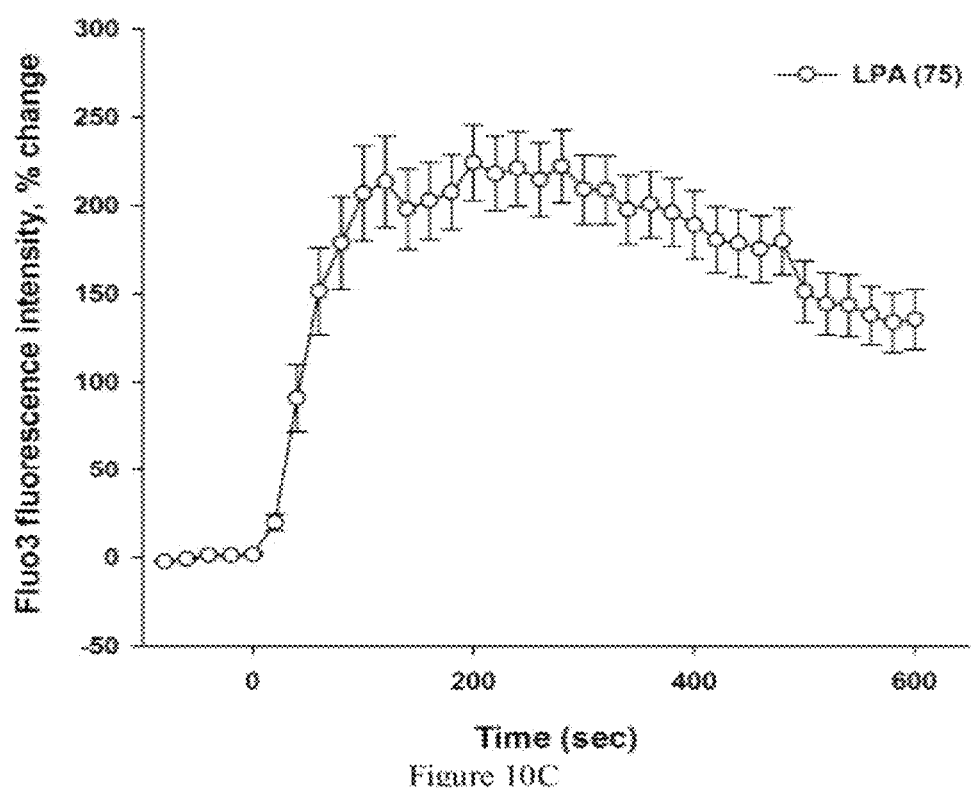

Deoxygenation-activated flickering cation conductance observed in human SS cells contrasted with the prolonged channel openings produced by 5 μM LPA (FIG. 10A). In SS cells, LPA increased NPo 16-fold, from 0.04±0.03 to 0.82±0.18 (n=8, p<0.001; Na methanesulfonate in bath and pipette, -Vp=-50 mV; FIG. 10B). LPA-induced cation conductance was 96% inhibited by 100 uM dipyridamole in the pipette, and 97% inhibited by 1 µM GsMTx-4 in the pipette (both n=4).

Carbon monoxide (CO) exposure prevents activation of cation conductance by deoxygenation in cell-attached patches on SS cells. Deoxy-HbSS polymerization is prevented by CO liganding with heme, stabilizing HbS tetrameric structure. As shown in FIG. 6D, prior CO exposure of SS cells prevented activation of conductance in on-cell patches upon deoxygenation. The normoxic NPo of 0.0377±0.0375 in CO-pretreated cells did not increase upon deoxygenation (NPo=0.0625±0.0375, n=4, P>0.05). Thus, prevention of deoxygenation-induced HbS polymerization was associated with inhibition of deoxygenation-stimulated channel activity.

Figure 7A:
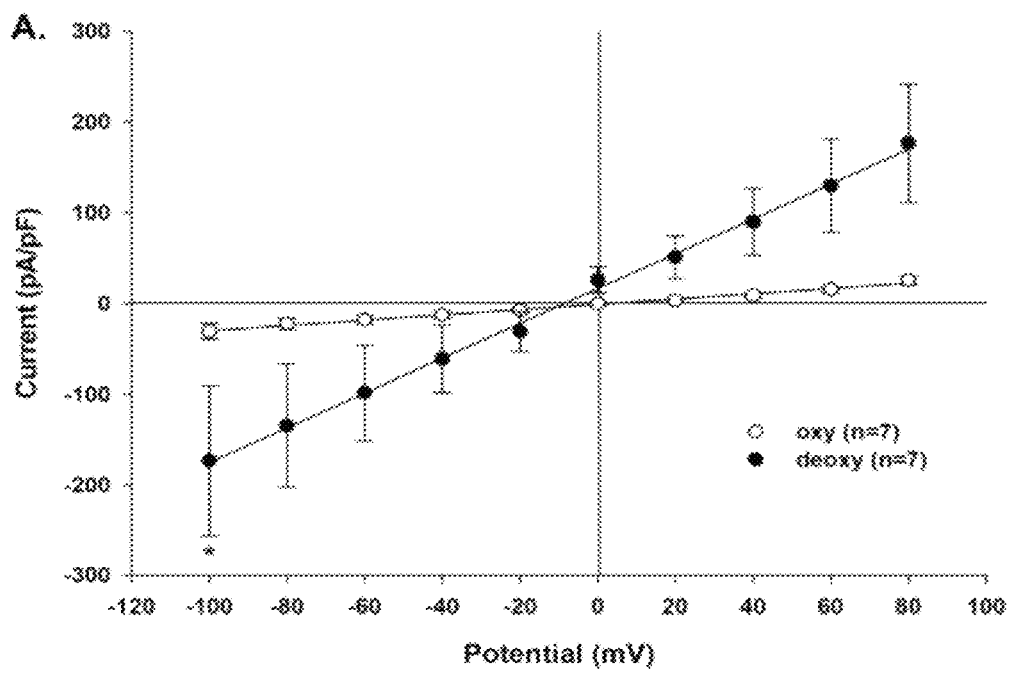
FIG. 7. A. Capacitance-normalized whole cell currents in nystatin-permeabilized patches on intact SAD mouse red cells recorded first in room air (oxy) and then in deoxygenated conditions (deoxy; *, p=0.016, Wilcoxon; n=7). B. Capacitance-normalized currents in nystatin-permeabilized patches on intact human SS cells recorded first in room air (oxy) and then in deoxygenated conditions (deoxy; *, p=0.031, Wilcoxon; n=6). In both cell types, symmetric pipette and bath solutions contained 150 mM Na methanesulfonate. Values are means+s.e.m.
Figure 7B:
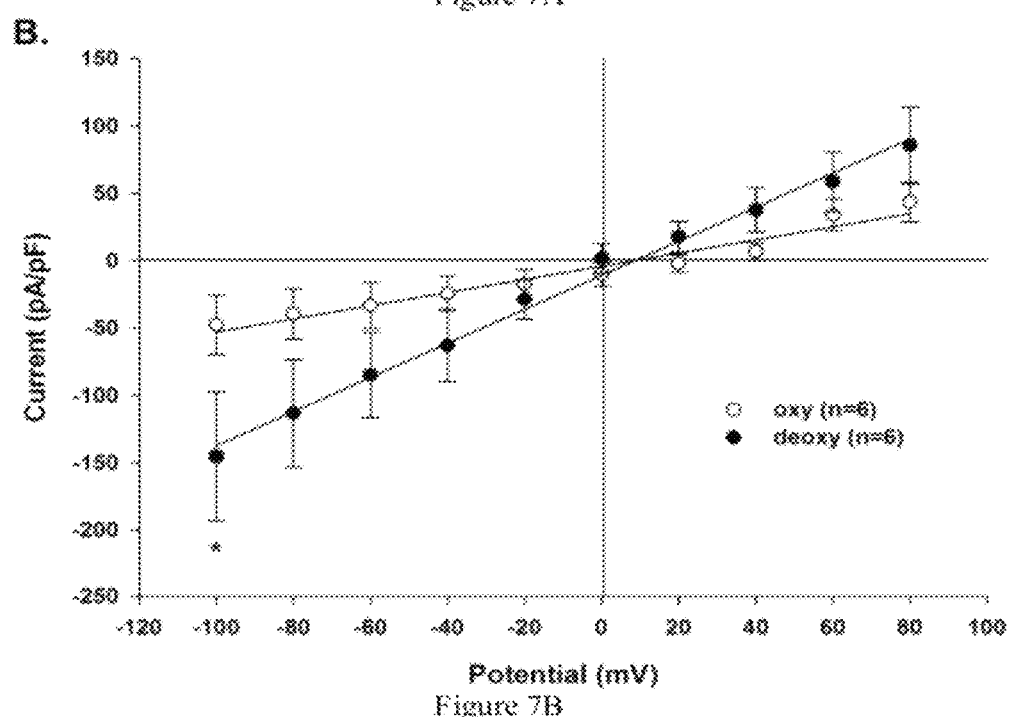

Deoxygenation activates whole cell conductance in nystatin-permeabilized patches of mouse SAD sickle red cells and human SS red cells: To extend our on-cell patch results, we examined whole cell cation currents using the nystatin-permeabilized patch configuration in individual cells monitored sequentially in room air followed by deoxygenation, with symmetric Na methanesulfonate in the pipette and the bath. SAD red cells (FIG. 7A) increased inward current at -100 mV holding potential from -31±9 nA in room air to -173±82 nA after deoxygenation (n=7, p=0.016). Human SS cells (FIG. 7B) increased inward current at -100 mV from -48±22 nA in room air to -145±48 nA after deoxygenation (n=6 p=0.031). In both cell types, deoxygenation-induced currents were ohmic. Thus, whole cell currents recorded in nystatin-permeabilized on-cell patches of human SS and of mouse SAD sickle red cells demonstrated stimulation upon deoxygenation (FIG. 7). The whole cell conductances estimated from nystatin-permeabilized patch records from oxygenated and deoxygenated human SS cells of 135 µm$^2$ nominal surface area were $1.0 \times 10^{-3}$ µS Cm$^{-2}$ and $2.4 \times 10^{-3}$ µS cm$^{-2}$, respectively. SAD mouse red cells with nominal surface area of 90 µm$^2$ exhibited respective values of 1.3×10-3 µS cm$^{-2}$ and $9.6 \times 10^{-3}$ µS cm$^{-2}$ (FIG. 7). These conductances are 2 orders of magnitude higher than previously estimated in intact human red cells from valinomycin-limited efflux or cell volume change, or from voltage-sensitive fluorescent dyes (Alper et al., 2008, *Blood Cells Molecules and Diseases* 41, 22-34).

Figure 8:
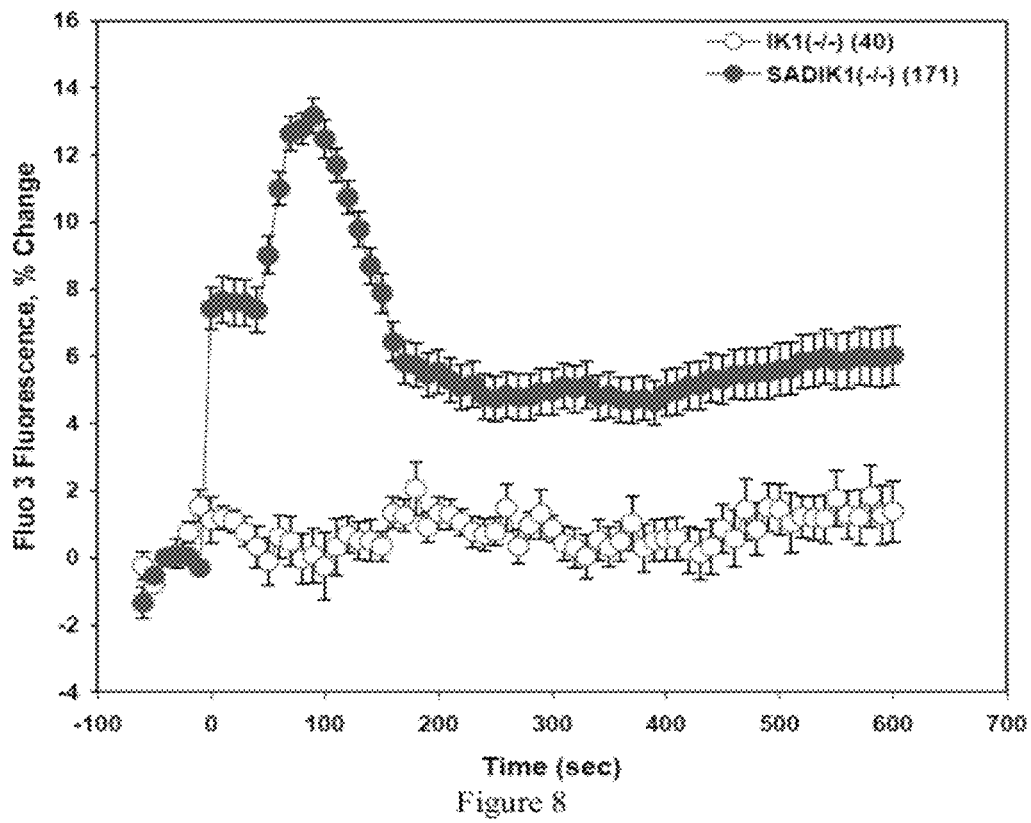
FIG. 8. Deoxygenation elevates [Ca2+]i in SAD sickle red cells in the absence of Kcnn4/KCa3.1/IK1 "Gardos channel". Fluo-3-loaded SAD red cells were subjected to deoxygenation at t=0. Whereas red cells with normal mouse hemoglobin that lacked KCa3.1 [IK1(-/-)] showed no change in [Ca2+]i, SAD red cells lacking KCa3.1 [SADIK1(-/-)] responded to deoxygenation with a substantial increase in [Ca2+]i that later fell to a sustained value ~50% of peak levels. Values are means+s.e.m. for (n) red cells from two mice studied in two experiments.

Kcnn4 is not required for deoxygenation-induced $[Ca^{2+}]_i$ elevation: Deoxygenation-induced elevation of $[Ca^{2+}]_i$ might require or be sustained by membrane hyperpolarization caused by KCa3.1 activation. Moreover, the elevated Fluo-3 fluorescence intensity suggestive of elevated $[Ca^{2+}]_i$ could be influenced by KCa3.1-mediated cell shrinkage of later onset. However, the hypoxia-induced 17% increase in Fluo-3 fluorescence intensity within 2-3 min in human SS red cells (FIG. 4B) is greater than can be simply explained by SS discocyte shrinkage in Cl$^-$ medium containing 1 mM Ca$^{2+}$ during 3 min anoxia at 37° C. (Lew et al. 1997, *J. Clin. Invest.*, 99(11), 2727-2735). We nonetheless examined the response to deoxygenation of red cells from SAD/kcnn4-/- mice genetically lacking the Kcnn4/IK1/KCa3.1 K$^+$ channel. The normal MCV reduction elicited in wildtype mouse red cells by exposure to A23187 in Ca$^{2+}$-containing medium (Brugnara et al. 1993) was abolished in red cells from both kcnn4-/- mice (Begenisich et al. 2004, *J. Biol. Chemisry*, 279(46):47681-47687) and from SAD/kcnn4-/- mice (data not shown). The absence of KCa3.1 in otherwise normal mouse red cells had no effect on the lack of deoxygenation-sensitive $[Ca^{2+}]_i$ elevation. In contrast, SAD/kcnn4-/- red cells elevated $[Ca^{2+}]_i$ in response to deoxygenation (FIG. 8), as did SAD red cells (FIG. 2D). However, shortly after achieving peak $[Ca^{2+}]_i$, SAD/kcnn4-/- red cells exhibited a fall in $[Ca^{2+}]_i$ to a value (FIG. 8) approximately 50% that of SAD cells (FIG. 2D). This lower plateau value may represent reduced driving force for Ca$^{2+}$ entry through the Psickle-like deoxygenation-induced permeability pathway in the less hyperpolarized state of cells lacking KCa3.1.

Example 2

This example describes toxicity studies with GsMTx-4. In one experiment, D-GsMTx4 was administered to 60 mdx mice and controls by daily subQ dosing at 5 mg/kg for 30 days at the Washington D.C. Wellstone center. No apparent toxicity with daily subQ dosing at 5 mg/kg was observed.

In another experiment, mice were IV injected with D-GsMTx4 at 9, 5, 3, and 1 mg/kg concentrations and observed for 1 hour at Covance Drug Development Company. There were 3 mice injected per concentration. No animals died, however at the highest dose (9 mg/kg) slight tremors and decreased activity was noted for ~0.5 hrs after injection. All mice appeared normal by 1 hour.

In another experiment, rats were IV injected with D-GsMTx4 at 9, 3, and 1 mg/kg concentrations and observed for 1 hour at Covance Drug Development Company. There were 3 rats injected for 3 and 1 mg/kg and 1 rat injected for 9 mg/kg concentration. No animals died. Highest dose of 9 mg/kg produced slow respiration, refusal to ambulate, decreased muscle tone that remained for the 60 minute test duration.

In another study, Cardiovascular hemodynamics and EKG was assessed after IV injection of D-GsMTx4 into telemetered free ranging ferrets in 4 cohorts of 3 animals over concentration ranging from 0.2 to 5 mg/kg at Covance Drug Development Company. This study was one of the main recommendations given us by the TACT advisory panel in Spring 2011. Particular attention was given to QT intervals, arterial pressure (mean, systolic and diastolic) and core temperature for 24 hours following IV injection. No statistically significant changes in any of the variables at any concentration were observed. There were also no behavior changes noted.

Example 3

This example describes the tissue distribution of GsMTx-4. Mice were dosed with D-GsMTx4 by three methods of administration and sacrificed at different time points over 24 hrs by Covance Drug Development Company. Tissues were harvested and sent frozen to Custom Biologics Company for concentration analysis. There were three animals per cohort and 7 time points distributed approximately logarithmically over 24 hours following a single dosing. We followed the distribution of peptide for three routes of administration -5 mg/kg IV, 50 mg/kg subQ and 50 mg/kg GI lavage. No animals died during the 24 hour experiment. We sampled 7 different tissues including EDL muscle, diaphragm, brain, bladder, heart, liver and blood. Both IV and subQ methods produced comparable distributions relative to the concentrations injected. Under both methods the peptide peaked in all tissues at about 2 hrs and plateaued for the 24 hr experiment duration. The blood concentrations for both methods peaked within 2 hrs and then decreased exponentially over 24 hrs. The distribution followed a pattern reflecting the relative capillary permeability of the tissue. So liver received the most while brain received the least. For the subQ method, muscle tissues all showed concentrations with the range predicted to be effective for MD treatment. The GI lavage produced almost no measurable concentration in any tissues. The data suggests that the effective half life of bound drug is very long and that should reduce the amount of drug required for chronic therapy, reducing costs. Since the peptide has a strong partition coefficient to lipids, the mean concentration in the tissues is much lower than that in the membrane, the site of action.

While specific embodiments have been presented in this description, those skilled in the art will recognize that routine modifications can be made by those skilled in the art without departing from the scope of the invention.

We claim:

1. A method of reducing deoxygenation induced calcium and cation permeable conductance of red blood cells of an individual who has sickle cell anemia comprising exposing the red blood cells of the individual who has been identified as having sickle cell anemia to a composition comprising an amount of an isolated or synthesized peptide comprising the sequence of SEQ ID NO: 1 that is effective to reduce deoxygenation induced calcium and cation permeable conductance of the red blood cells.

2. The method of claim 1, wherein the red blood cells are exposed in vivo by administering to an individual a composition comprising the peptide in a pharmaceutically acceptable carrier at an amount effective to reduce deoxygenation induced calcium and cation permeable conductance.

3. The method of claim 2, wherein the peptide is administered such that the level of said peptide in blood is from 0.1 to 10 micromolar.

4. The method of claim 3, wherein the level of the peptide in blood is from 0.1 to 5.0 micromolar.

5. The method of claim 2, wherein the peptide is administered via a route selected from the group consisting of intravenous, oral, subcutaneous, intramuscular and mucosal.

6. The method of claim 2, wherein the composition is administered to the individual daily.

7. A method of reducing the severity of sickle cell anemia comprising exposing red blood cells of an individual afflicted with sickle cell anemia to a peptide comprising the sequence of SEQ ID NO: 1 in a pharmaceutically acceptable carrier in an amount effective to reduce one or more symptoms of sickle cell anemia.

8. The method of claim 2, wherein the red blood cells are exposed in vivo by administering to the individual a composition comprising D-enantiomer of the peptide.

* * * * *

```
                            SEQUENCE LISTING

<160> NUMBER OF SEQ ID NOS: 5

<210> SEQ ID NO 1
<211> LENGTH: 34
<212> TYPE: PRT
<213> ORGANISM: Grammastola spatulata

<400> SEQUENCE: 1

Gly Cys Leu Glu Phe Trp Trp Lys Cys Asn Pro Asn Asp Asp Lys Cys
1               5                   10                  15

Cys Arg Pro Lys Leu Lys Cys Ser Lys Leu Phe Lys Leu Cys Asn Phe
            20                  25                  30

Ser Phe

<210> SEQ ID NO 2
<211> LENGTH: 34
<212> TYPE: PRT
<213> ORGANISM: artificial sequence
<220> FEATURE:
<223> OTHER INFORMATION: variable peptide sequence based on Grammastola
      spatulata mechanotoxin4
<220> FEATURE:
<221> NAME/KEY: misc_feature
<222> LOCATION: (32)..(34)
<223> OTHER INFORMATION: Xaa can be any naturally occurring amino acid

<400> SEQUENCE: 2

Gly Cys Leu Glu Phe Trp Trp Lys Cys Asn Pro Asn Asp Asp Lys Cys
1               5                   10                  15

Cys Arg Pro Lys Leu Lys Cys Ser Lys Leu Phe Lys Leu Cys Asn Xaa
            20                  25                  30

Xaa Xaa

<210> SEQ ID NO 3
<211> LENGTH: 34
<212> TYPE: PRT
<213> ORGANISM: artificial sequence
<220> FEATURE:
<223> OTHER INFORMATION: Grammastola spatulata mechanotoxin4 variant

<400> SEQUENCE: 3

Gly Cys Leu Glu Phe Trp Trp Lys Cys Asn Pro Asn Asp Asp Lys Cys
1               5                   10                  15

Cys Arg Pro Lys Leu Lys Cys Ser Lys Leu Phe Lys Leu Cys Asn Tyr
            20                  25                  30

Ser Phe

<210> SEQ ID NO 4
<211> LENGTH: 34
<212> TYPE: PRT
<213> ORGANISM: artificial sequence
<220> FEATURE:
<223> OTHER INFORMATION: Grammastola spatulata mechanotoxin4 variant

<400> SEQUENCE: 4
```

```
Gly Cys Leu Glu Phe Trp Trp Lys Cys Asn Pro Asn Asp Asp Lys Cys
1               5                   10                  15
Cys Arg Pro Lys Leu Lys Cys Ser Lys Leu Phe Lys Leu Cys Asn Phe
            20                  25                  30
Cys Phe

<210> SEQ ID NO 5
<211> LENGTH: 35
<212> TYPE: PRT
<213> ORGANISM: artificial sequence
<220> FEATURE:
<223> OTHER INFORMATION: Grammastola spatulata mechanotoxin4 variant

<400> SEQUENCE: 5

Gly Cys Leu Glu Phe Trp Trp Lys Cys Asn Pro Asn Asp Asp Lys Cys
1               5                   10                  15
Cys Arg Pro Lys Leu Lys Cys Ser Lys Leu Phe Lys Leu Cys Asn Phe
            20                  25                  30
Ser Ser Ala
        35
```